United States Patent [19]

Naito et al.

[11] Patent Number: 5,651,919

[45] Date of Patent: Jul. 29, 1997

[54] BENZYL ETHER DERIVATIVE AND COMPOSITION CONTAINING THE SAME

[75] Inventors: Tomijiro Naito; Yumiko Sakamaki, both of Saitama-ken; Hisato Sato, Tokyo, all of Japan

[73] Assignee: Citizen Watch Co., Ltd., Tokyo, Japan

[21] Appl. No.: 596,373

[22] PCT Filed: Jun. 20, 1995

[86] PCT No.: PCT/JP95/01226

§ 371 Date: Feb. 23, 1996

§ 102(e) Date: Feb. 23, 1996

[87] PCT Pub. No.: WO96/00204

PCT Pub. Date: Jan. 4, 1996

[30] Foreign Application Priority Data

| | | | |
|---|---|---|---|
| Jun. 23, 1994 | [JP] | Japan | 6-141842 |
| Nov. 4, 1994 | [JP] | Japan | 6-271031 |
| Nov. 18, 1994 | [JP] | Japan | 6-284643 |
| Mar. 9, 1995 | [JP] | Japan | 7-049469 |

[51] Int. Cl.$^6$ .................... G09K 19/30; G02F 1/13; C07C 43/00; C07C 25/13
[52] U.S. Cl. ............... 252/299.63; 250/299.66; 568/669; 570/127; 570/130; 349/182
[58] Field of Search ............. 252/299.01, 299.63, 252/299.66; 359/103; 568/669; 570/127, 130

[56] References Cited

U.S. PATENT DOCUMENTS

| | | | |
|---|---|---|---|
| 4,400,293 | 8/1983 | Römer et al. | 252/299.63 |
| 5,032,313 | 7/1991 | Goto et al. | 252/299.63 |
| 5,478,495 | 12/1995 | Terada et al. | 252/299.01 |

FOREIGN PATENT DOCUMENTS

| | | |
|---|---|---|
| 4334362 | 4/1995 | Germany. |
| 9510496 | 4/1995 | WIPO. |

*Primary Examiner*—Shean C. Wu
*Attorney, Agent, or Firm*—Oblon, Spivak, McClelland, Maier & Neustadt, P.C.

[57] ABSTRACT

Disclosed are a benzyl ether derivative represented by the following formula (I), useful as a liquid crystal display material, and a liquid crystal composition containing the same and a liquid crystal display device utilizing the composition.

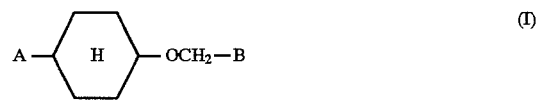

[wherein A represents a 4-alkylcyclohexyl group or an alkyl group, B represents a di- or tri-fluorophenyl group, a 4-(di- or tri-fluorophenyl)phenyl group, a 4-alkylphenyl group or a 4-alkoxyphenyl group].

The compound (I) of the present invention has good compatibility with other compounds, and can be used in a liquid crystal composition by combining with many liquid crystal materials as a constitutional component of the liquid crystal composition. It has functions of lowering a C-N point of a liquid crystal composition, lowering a threshold voltage by enlarging a dielectric anisotropy, and also lowering a viscosity and increasing a N-I point of the liquid crystal composition. Further, according to selection thereof, it is also possible to change an optical anisotropy, and can be advantageously used for improving characteristics of a liquid crystal composition particularly for a TN type, STN type or active type liquid crystal display device.

17 Claims, 18 Drawing Sheets

5,651,919

BENZYL ETHER DERIVATIVE AND COMPOSITION CONTAINING THE SAME

TECHNICAL FIELD

This application is a 371 PCT/JP 95/01226 filed Jun. 20, 1995

This invention relates to a benzyl ether derivative, more specifically it relates to a benzyl ether derivative available as a liquid crystal display material and a liquid crystal composition containing the same, and a liquid crystal display device utilizing said composition.

BACKGROUND ART

A liquid crystal display device has been widely utilized for a watch, an electronic calculator as well as a word processor, a television set, etc. Of these liquid crystal display device, particularly frequently used is a TN type (twisted nematic type) liquid crystal display device which utilizes optical anisotropy and dielectric anisotropy of a liquid crystal material.

At present, as characteristics required for a liquid crystal material to be used for liquid crystal display devices, there may be mentioned that a crystal-nematic point (C-N point) is low and a nematic-isotropic liquid point (N-I point) is high in order to have a wide liquid crystal temperature range, a viscosity is low in order to obtain a rapid electro-optical response rate, an optical anisotropy ($\Delta n$) is coincide with the constitution of a panel in order to have a wide visual scope, a dielectric anisotropy ($\Delta \epsilon$) is large to lower a driving voltage, and it is chemically and optically stable.

Until now, any single liquid crystal compound satisfying all the characteristics as mentioned above has not yet been found. Thus, it is the present status that several kinds of liquid crystal compounds having various characteristics are mixed or further various kinds of non-liquid crystal compounds are mixed for practical use.

Also, depending on the liquid crystal display device, degree of the above characteristics to be required is different so that development of a novel liquid crystal compound providing characteristics suitable for the objects of a liquid crystal display device is required.

Heretofore, as a benzyl ether series compound to be used as a liquid crystal composition, there have been known trans-4-(trans-4-alkylcyclohexyl)cyclohexyl-4-substituted benzyl ether substituted by CN, F, Cl or Br (Japanese Patent Publication No. 50734/1991) or trans-4-(trans-4-alkenylcyclohexyl)cyclohexyl-3,4-di-substituted benzyl ether substituted by F or Cl (Japanese Laid-Open Patent Application No. 157925/1989), and further trans-4-alkylcyclohexyl-4-substituted benzyl ether (Japanese Patent Publication No. 14088/1992).

However, other benzyl ether compound than the above such as, for example, a compound wherein a straight alkylcyclohexyl group or a straight alkylbicyclohexyl group is bonded to a difluorobenzyl ether has never been known.

As described above, a compound which satisfy all the characteristics required for a liquid crystal material has not been found at the present stage, and even when various liquid crystal compounds or non-liquid crystal compounds are used in combination, there is no material which satisfies the above characteristics sufficiently. In addition, each of these compounds has merits and demerits in their characteristics. Therefore, as mentioned above, it is present status that various liquid crystal and non-liquid crystal compounds are used in combination for practical use, and thus, more excellent novel liquid crystal compounds are required to be provided.

DISCLOSURE OF THE INVENTION

The present inventors have synthesized various kinds of novel benzyl ether derivatives to investigate characteristics thereof as a liquid crystal compound. As the results, they have found that the compound represented by the following formula (I) could lower the threshold voltage and lower the driving voltage, improve liquid crystal characteristics at lower temperatures by lowering a crystal-nematic initiating point, and also it has an effect of increasing a N-I point without increasing the viscosity of the liquid crystal composition or an effect of changing optical anisotropy, and yet it has a large compatibility with various compounds and has excellent characteristics as a liquid crystal material or a liquid crystal additive component whereby they have accomplished the present invention.

That is, an object of the present invention is to provide a benzyl ether derivative represented by the following formula (I):

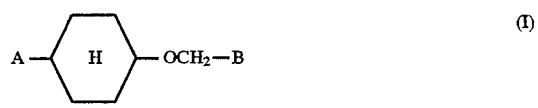

[wherein A represents a 4-alkylcyclohexyl group or an alkyl group, B represents a di- or tri-fluorophenyl group, a 4-(di- or tri-fluorophenyl)phenyl group, a 4-alkylphenyl group or a 4-alkoxyphenyl group] which is useful as a liquid crystal material or a liquid crystal additive component.

Another object of the present invention is to provide a composition which is useful as a liquid crystal composition containing the above benzyl ether derivative (I).

BEST MODE FOR PRACTICING THE INVENTION

Figure 1:
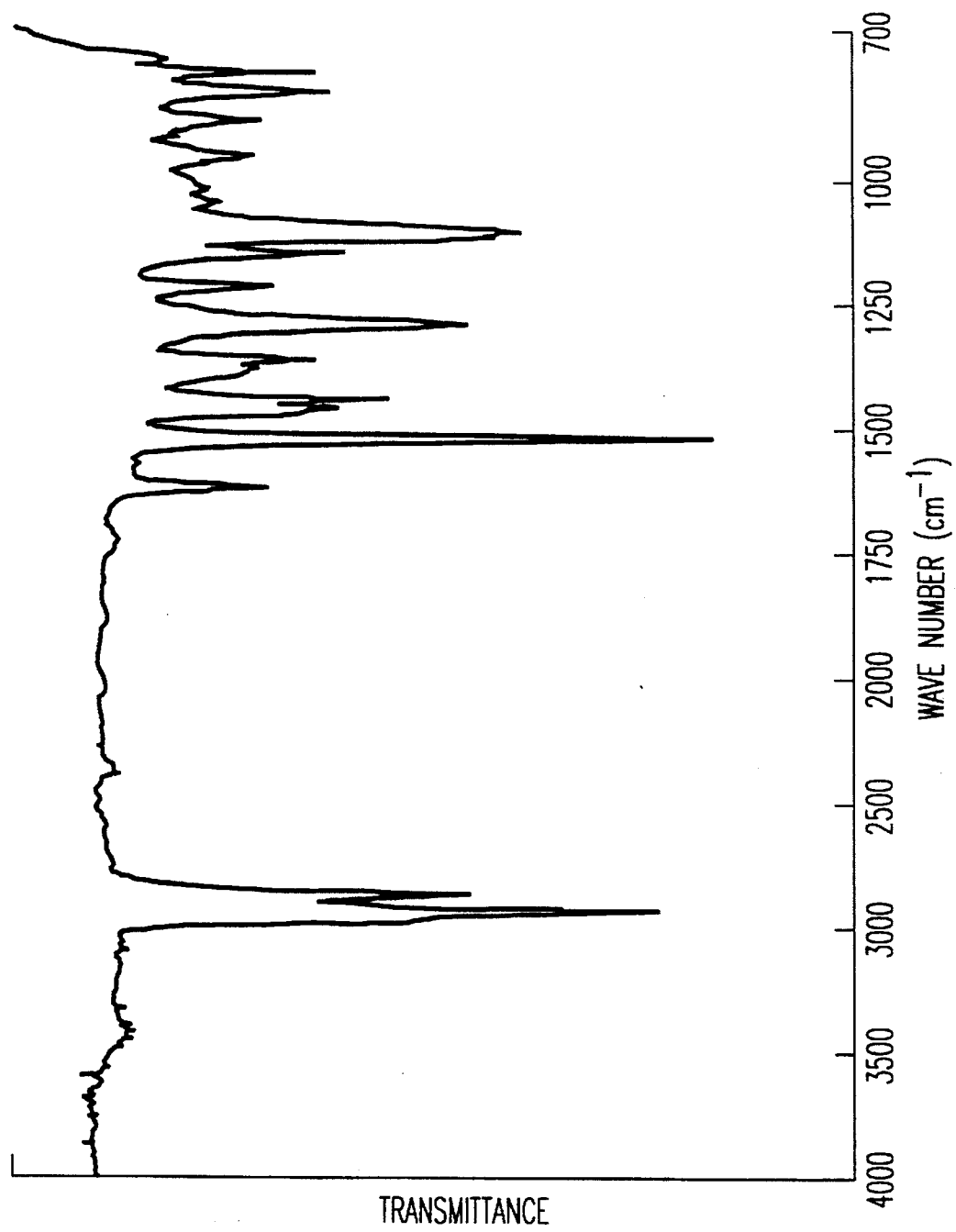
FIG. 1 is a diagram showing an infrared absorption spectrum of trans-4-propylcyclohexyl-3,4-difluorobenzyl ether of the present invention.

In the benzyl ether derivative (I) of the present invention, as the alkyl group of the group A and the alkyl group in the 4-alkylcyclohexyl group, there may be preferably mentioned an alkyl group having 1 to 7 carbon atoms such as a methyl group, an ethyl group, a propyl group, a butyl group, a pentyl group, a hexyl group, a heptyl group, etc. Among these, those having 3 to 5 carbon atoms are particularly preferred. These alkyl groups may be branched.

Also, as the alkyl group in the 4-alkylphenyl group of the group B, those as described above are also mentioned, and as the alkoxy group of the 4-alkoxyphenyl group, there may be preferably mentioned an alkoxy group having 1 to 7 carbon group such as a methoxy group, an ethoxy group, a propoxy group, a butoxy group, a pentyloxy group, a hexyloxy group, a heptyloxy group, etc. Among these, those having 1 to 3 carbon atoms are particularly preferred. These alkoxy groups may also be branched.

Further, as the di- or trifluorophenyl group and the di- or trifluorophenyl group of the 4-(di- or trifluorophenyl) group of the group B, there may be mentioned 3,4-difluorophenyl group, 2,3-difluorophenyl group, 2,4-difluorophenyl group, 2,3,4-trifluorophenyl group, etc.

The benzyl ether derivative (I) of the present invention can be prepared, for example, by reacting a 4-substituted cyclohexanol (II) and a halogenated benzyl derivative (III) according to the following formula:

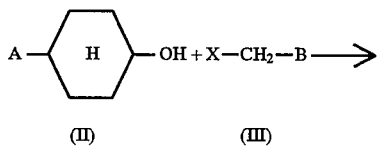

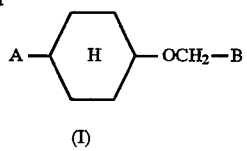

(wherein X represents a halogen atom, A and B have the same meanings as defined above).

The above reaction can be carried out in a suitable solvent such as N,N-dimethylformamide, tetrahydrofuran, etc. in the presence of a coupling catalyst such as sodium hydride, etc. This reaction may be carried out at a temperature of room temperature to a reflux temperature of the solvent, preferably 50° to 70° C. or so for 1 to 24 hours or so, preferably 4 to 12 hours or so.

Among the starting materials of the above reaction, 4-substituted cyclohexanols (II) are compounds which are either known in the art or can be easily prepared according to the preparation method of the known compounds.

Also, most of the halogenated benzyl derivatives (III) which are another starting material are known in the art, but novel compounds such as a halogenated phenylbenzyl derivative represented by the following formula (IIIa):

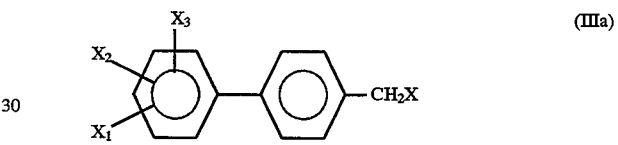

(wherein X represents a halogen atom, and at least two of $X_1$, $X_2$ and $X_3$ represent fluorine atoms, and the remaining one represents a hydrogen atom or a fluorine atom) can be prepared from a halogenated biphenyl compound (IV), for example, by the following formula:

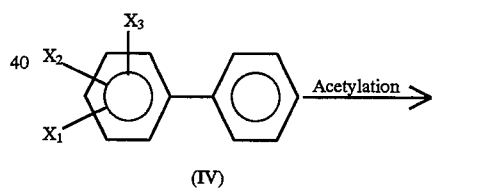

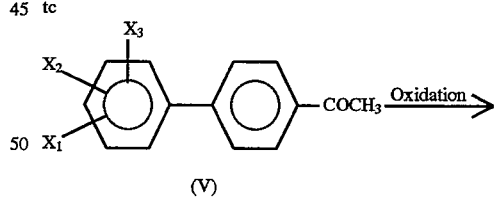

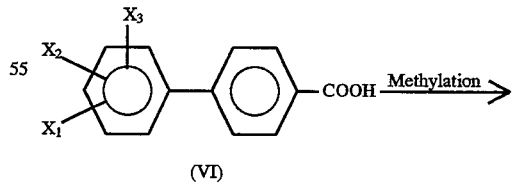

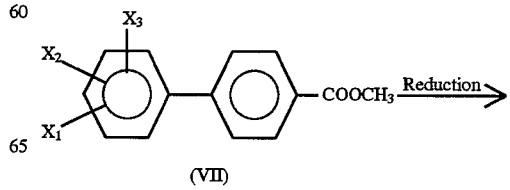

-continued

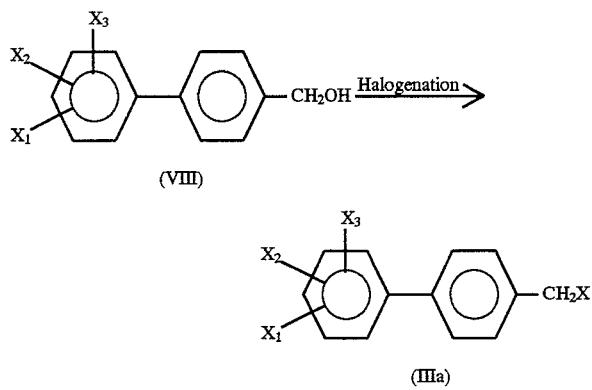

(wherein X, $X_1$, $X_2$ and $X_3$ have the same meanings as defined above).

That is, the known di- or trifluorobiphenyl (IV) is subjected to acetylation and then oxidation to obtain a compound (VI). Then, the resulting compound is Subjected to methylation and reduction to obtain a compound (VIII) and finally the hydroxyl group of the compound (VIII) is halogenated to obtain the desired halogenated phenylbenzyl derivative (IIIa). For each of the processing steps of these reactions, methods well known in the art can be utilized.

The compounds of the present invention obtained as mentioned above can be used as a liquid crystal material or a liquid crystal additive component after purification by the known method, if necessary.

The compounds of the present invention thus obtained can be classified into the compounds represented by the following formulae.

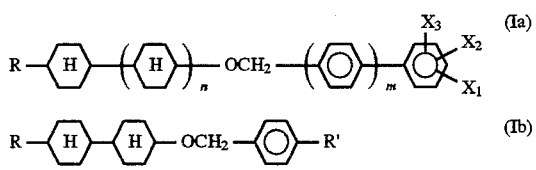

(wherein R represents an alkyl group, R' represents an alkyl group or an alkoxy group, at least two of $X_1$, $X_2$ and $X_3$ represent fluorine atoms, and another one represents a hydrogen atom or a fluorine atom, and n and m each represent an integer of 0 or 1)

Of these, many of the benzyl ether derivatives containing a halogen represented by the formula (Ia) have an action of lowering Δn and increasing a N-I point of a liquid crystal composition and enlarge dielectric anisotropy. Also, among the benzyl ether derivatives (Ia), there are compounds having an action of decreasing the viscosity or a C-N point. In the above formula (Ia), the compound wherein n and m are both 1 has an action of increasing Δn contrary to the other compounds.

On the other hand, in the benzyl ether derivatives represented by the formula (Ib), when a straight chain alkyl group is selected as the terminal alkyl group or alkoxy group represented by R', the compound has excellent liquid crystallinity than the compounds described in the prior art since it has a rod-like shape molecule. Thus, when it is formulated in a liquid crystal composition, it has a function of increasing a N-I point of the liquid crystal composition and also has a function of lowering Δn.

The benzyl ether derivatives (I) of the present invention are each having excellent characteristics as a constitutional component of the liquid crystal composition. Also, they have large compatibility with a wide range of liquid crystal materials whereby they are miscible with many liquid crystal compounds to form a liquid crystal composition.

As the liquid crystal compounds miscible with the benzyl ether derivatives (I) of the present invention, there may be mentioned liquid crystal compounds such as an ester type, a cyclohexylphenyl type, a biphenyl type, a pyrimidine type, a dioxane type, a tolan type, etc.

Also, the benzyl ether derivatives (I) of the present invention may be mixed with each other to produce a liquid crystal composition.

When the benzyl ether derivatives (I) of the present invention is mixed with other liquid crystal compounds to produce a liquid crystal composition, the formulating amount thereof cannot be determined indiscriminately and varies depending on the kind of the other liquid crystal compound, formulation of the liquid crystal composition and an object of use of the liquid crystal composition, but generally, in the liquid crystal composition, 5 to 80% by weight, more preferably 10 to 50% by weight.

Action

A driving voltage of a liquid crystal display device depends on the value of a threshold voltage Vth, and by making the threshold voltage Vth small, the liquid crystal display device can be driven with a lower voltage. The threshold voltage Vth is inversely proportional to the square root of the dielectric anisotropy Δε so that when a liquid crystal material having a positive dielectric anisotropy Δε is used, the threshold voltage Vth can be controlled to a low value whereby the driving voltage can be made low.

The reason why the driving voltage can be decreased by using the benzyl ether derivative (Ia) containing fluorine of the present invention can be considered as the result that the dielectric anisotropy Δε becomes large by addition of these compounds whereby the threshold voltage Vth becomes low.

Also, a practically used liquid crystal composition is generally prepared by mixing a compound having a liquid crystal phase at a neighbor of room temperature and a compound having a liquid crystal phase at a temperature region higher than room temperature. In order to use a liquid crystal display device out of doors, the liquid crystal composition should be present stably at the temperature range of $-40°$ C. to $90°$ C. Also, due to temperature dependencies of dielectric anisotropy and optical anisotropy, i.e., at around N-I point, abrupt change occurs so that it is necessary to obtain a liquid crystal material having a high N-I point.

The reason why these conditions can be satisfied by formulating the benzyl ether derivatives (I) of the present invention in a liquid crystal composition can be considered that the compound (I) of the present invention markedly decreases a C-N point of the liquid crystal composition which makes the liquid crystal characteristics at low temperature good or a N-I point can be raised high by the excellent liquid crystallinity due to rod-like property of the alkyl group at the molecular terminals.

Also, a starting up time $\tau_{on}$ when a voltage is applied and a breaking down time $\tau_{off}$ when a voltage is cut off are given by the following formulae.

$$\tau_{on} = \eta_{ii} d^2 (\epsilon 0 \Delta \epsilon V^2 - K\pi^2)^{-1}$$

$$\tau_{off} = \eta_{ii} d^2 / \pi^2 K$$

Wherein, $\eta_{ii}$ is a parameter of a viscosity, d is a thickness of a liquid crystal layer, $\epsilon 0$ is a dielectric constant in vacuum, Δε is an anisotropy of the dielectric constant, V is an applied voltage, K is a parameter involving modulus of elasticity and $K=k11+(k33-2k22)/4$ (wherein k11, k22, k33 are each spray, twist and bend modulus of elasticities).

Thus, to make a response speed faster, it is indispensable that the liquid crystal material is low viscosity, i.e., a low viscosity liquid crystal compound has to be obtained.

The benzyl ether derivative (I) of the present invention has low viscosity as compared with a liquid crystal compound containing a cyano group so that a viscosity of a liquid crystal composition with a level for practical use can be lowered and an electro-optical response speed of a liquid crystal display device using the same can be made fast.

EXAMPLES

Next, the present invention is described in more detail by referring to Examples but the present invention is not limited by these Examples. In the present Examples, evaluation of low temperature characteristics of the compositions was carried out by cooling the composition to crystallize and then gradually raising the temperature and observing with eyes the point that the crystal begins to show fluidity, and the temperature at that time is called to a crystal-nematic starting point and abbreviated to as a C-Ns point. Also, a threshold voltage Vth shown in the present Examples is a value when the liquid crystal composition is mounted on a TN type liquid crystal display device with a cell thickness of 9 μm.

Example 1

0.6 g of sodium hydride (60%) was added to 30 ml of anhydrous N,N'-dimethylformamide. While stirring sufficiently, to the solution was added a solution of 2.13 g of trans-4-propylcyclohexanol dissolved in 10 ml of anhydrous N,N'-dimethylformamide. This mixture was continued to stirring at 50° C. for one hour and then 3.1 g of 3,4-difluorobenzyl bromide was added thereto, and the reaction was carried out at the same temperature for 3 hours with stirring. After completion of the reaction, 100 ml of water was added to the reaction mixture, the mixture was extracted with toluene, washed with a saturated NaCl aqua, dried and the solvent was removed under reduced pressure. The residue was purified by silica gel column to obtain 1.0 g of trans-4-propylcyclohexyl-3,4-difluorobenzyl ether.

Figure 2:
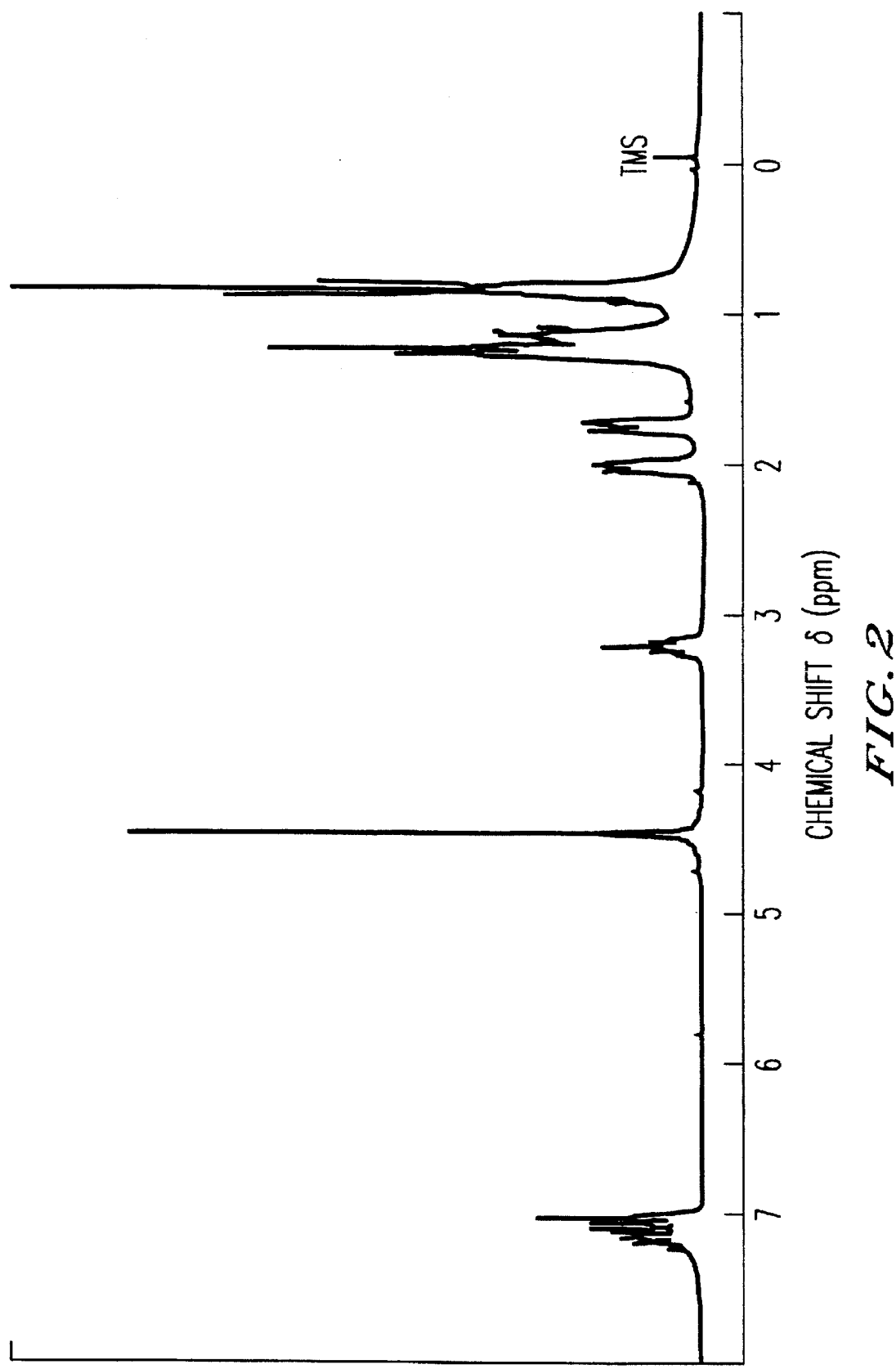
FIG. 2 is a diagram showing 1 H nuclear magnetic resonance spectrum of trans-4-propylcyclohexyl-3,4-difluorobenzyl ether of the present invention.

The resulting compound had a melting point of −1.3° C. Also, an infrared absorption spectrum and 1 H nuclear magnetic resonance spectrum of the compound were measured. The obtained infrared absorption spectrum is shown in FIG. 1 and $^1H$ nuclear magnetic resonance spectrum in FIG. 2.

The following compounds can be obtained according to the same treatment.

Trans-4-methylcyclohexyl-3,4-difluorobenzyl ether
Trans-4-ethylcyclohexyl-3,4-difluorobenzyl ether
Trans-4-butylcyclohexyl-3,4-difluorobenzyl ether
Trans-4-pentylcyclohexyl-3,4-difluorobenzyl ether
Trans-4-hexylcyclohexyl-3,4-difluorobenzyl ether
Trans-4-heptylcyclohexyl-3,4-difluorobenzyl ether
Trans-4-octylcyclohexyl-3,4-difluorobenzyl ether
Trans-4-nonylcyclohexyl-3,4-difluorobenzyl ether
Trans-4-decylcyclohexyl-3,4-difluorobenzyl ether

Example 2

In the same manner as in Example 1 except for using 3.36 g of trans-4-(trans-4-propylcyclohexyl)cyclohexanol in place of 2.13 g of trans-4-propylcyclohexanol, 1.8 g of trans-4-(trans-4-propylcyclohexyl)cyclohexyl-3,4-difluorobenzyl ether was obtained.

Figure 3:
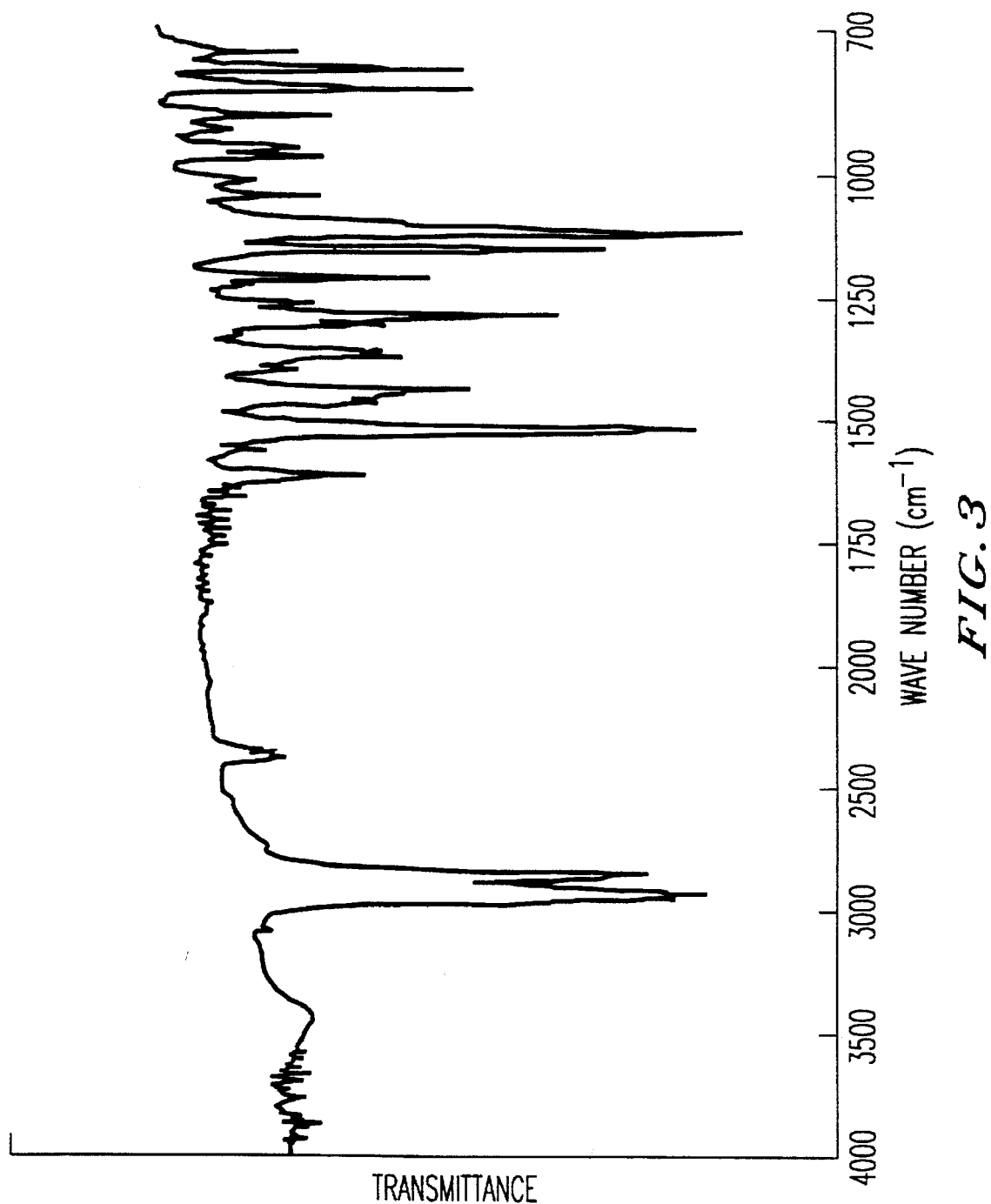
FIG. 3 is a diagram showing an infrared absorption spectrum of trans-4-(trans-4-propylcyclohexyl)cyclohexyl-3,4-difluorobenzyl ether of the present invention.
Figure 4:
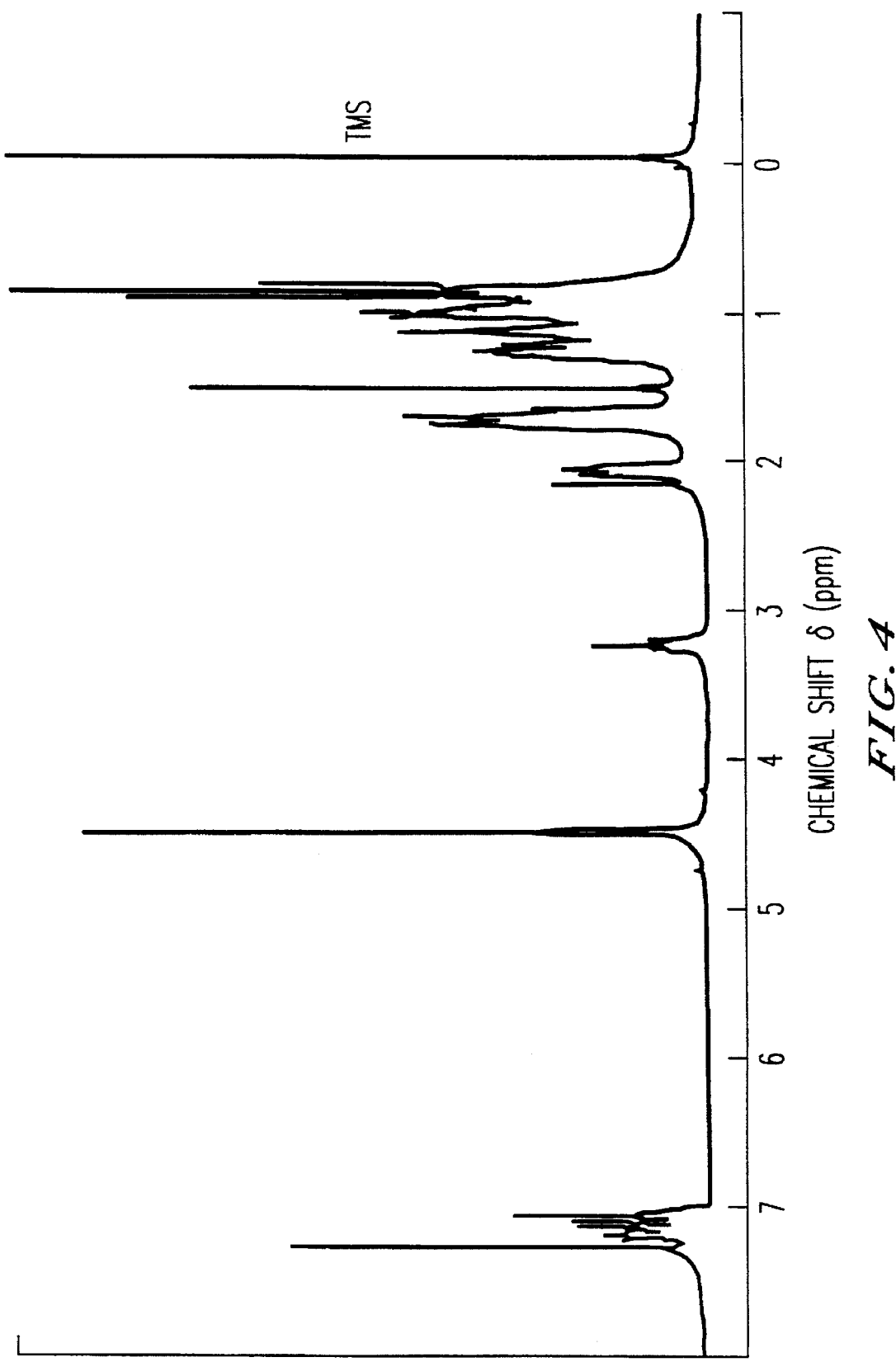
FIG. 4 is a diagram showing 1 H nuclear magnetic resonance spectrum of trans-4-(trans-4-propylcyclohexyl) cyclohexyl-3,4-difluorobenzyl ether of the present invention.

This compound is a nematic liquid crystal, and had a C-N point of 58.4° C. and a N-I point of 70.5° C. Also, an infrared absorption spectrum and 1H nuclear magnetic resonance spectrum of the compound were measured. The obtained infrared absorption spectrum is shown in FIG. 3 and 1H nuclear magnetic resonance spectrum in FIG. 4.

The following compounds can be obtained according to the same treatment.

Trans-4-(trans-4-methylcyclohexyl)cyclohexyl-3,4-difluorobenzyl ether
Trans-4-(trans-4-ethylcyclohexyl)cyclohexyl-3,4-difluorobenzyl ether
Trans-4-(trans-4-butylcyclohexyl)cyclohexyl-3,4-difluorobenzyl ether
Trans-4-(trans-4-pentylcyclohexyl)cyclohexyl-3,4-difluorobenzyl ether
Trans-4-(trans-4-hexylcyclohexyl)cyclohexyl-3,4-difluorobenzyl ether
Trans-4-(trans-4-heptylcyclohexyl)cyclohexyl-3,4-difluorobenzyl ether
Trans-4-(trans-4-octylcyclohexyl)cyclohexyl-3,4-difluorobenzyl ether
Trans-4-(trans-4-nonylcyclohexyl)cyclohexyl-3,4-difluorobenzyl ether
Trans-4-(trans-4-decylcyclohexyl)cyclohexyl-3,4-difluorobenzyl ether

Example 3

A liquid crystal composition was prepared by using a commercially available base liquid crystal composition (ZLI-1083, available from Merck Co.) containing the compound shown below and trans-4-propylcyclohexylhexyl-3,4-difluorobenzyl ether obtained in Example 1, and characteristics thereof were examined. The liquid crystal composition was prepared by adding 10 parts by weight of the compound obtained in Example 1 to 90 parts by weight of the base liquid crystal composition. As the results, while the characteristics of the base liquid crystal composition were a N-I point of 52° C., a C-Ns point of −10° C., Δn of 0.12, a viscosity of 23.0 cP and Vth of 1.58 V, the characteristics of the liquid crystal composition in which trans-4-propylcyclohexyl-3,4-difluorobenzyl ether was added to the base liquid crystal composition were a N-I point of 35.9° C., a C-Ns point of −22° C., Δn of 0.098, a viscosity of 21.4 cP and Vth of 1.24 V.

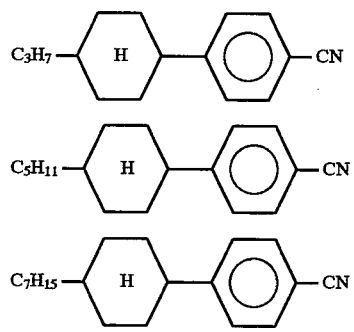

Example 4

To 90 parts by weight of the same base liquid crystal composition as in Example 3 was added 10 parts by weight of trans-4-(trans-4-propylcyclohexyl)cyclohexyl-3,4-difluorobenzyl ether obtained in Example 2 to obtain a liquid crystal composition. This liquid crystal composition had a N-I point of 52.8° C., a C-Ns point of −62° C., Δn of 0.114, a viscosity of 22.5 cP and Vth of 1.46 V.

Example 5

To 0.6 g of sodium hydride (purity 60%) was added 30 ml of anhydrous N,N-dimethylformamide. While stirring sufficiently, to the solution was added a solution of 3.36 g of trans-4-(trans-4-propylcyclohexyl)cyclohexanol dissolved in 10 ml of anhydrous N,N-dimethylformamide. This mixture was continued to stirring at 50° C. for one hour and then 3.0 g of 4-propylbenzyl chloride was added thereto, and the mixture was stirred and reacted at the same temperature for 3 hours with stirring. After completion of the reaction, 100 ml of water was added to the reaction mixture, the mixture was extracted with toluene, washed with a saturated NaCl aqua, dried and the solvent was removed under reduced pressure. The residue was purified by silica gel column to obtain 1.2 g of trans-4(trans-4-propylcyclohexyl)cyclohexyl-4-propylbenzyl ether.

Figure 5:
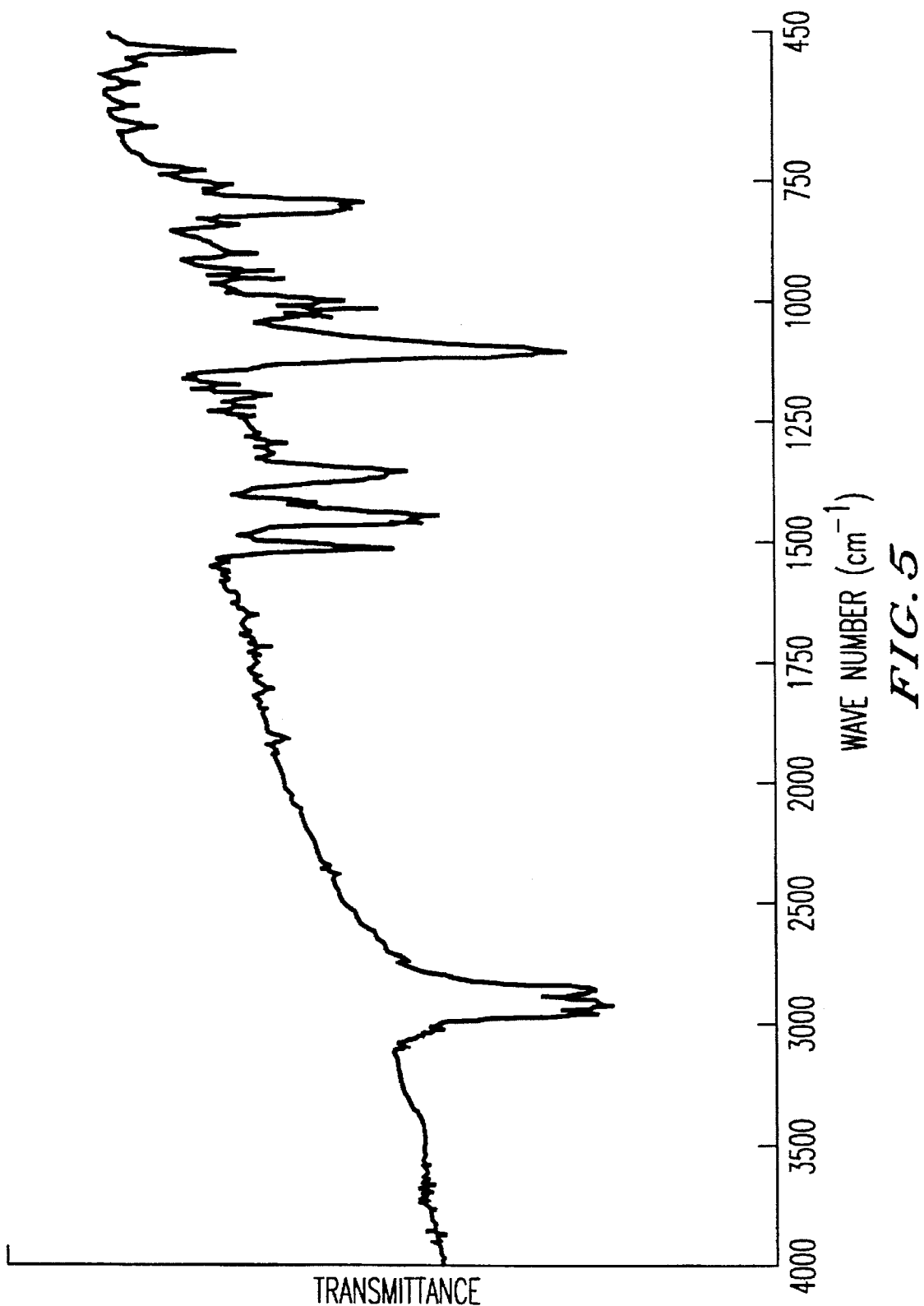
FIG. 5 is a diagram showing an infrared absorption spectrum of trans-4-(trans-4-propylcyclohexyl)cyclohexyl-4-propylbenzyl ether of the present invention.

The resulting compound is a smectic liquid crystal and had a C-S point (crystal-smectic point) of 45° C. and a S-I point (smectic-transparent point) of 101° C. Also, an infrared absorption spectrum of this compound is shown in FIG. 5.

Example 6

In the same manner as in Example 5 except for using 3.57 g of trans-4-(trans-4-butylcyclohexyl)cyclohexanol in place of 3.36 g of trans-4-(trans-4-propylcyclohexyl)cyclohexanol, 1.9 g of trans-4-(trans-4-butylcyclohexyl)cyclohexyl-4-propylbenzyl ether was obtained.

Figure 6:
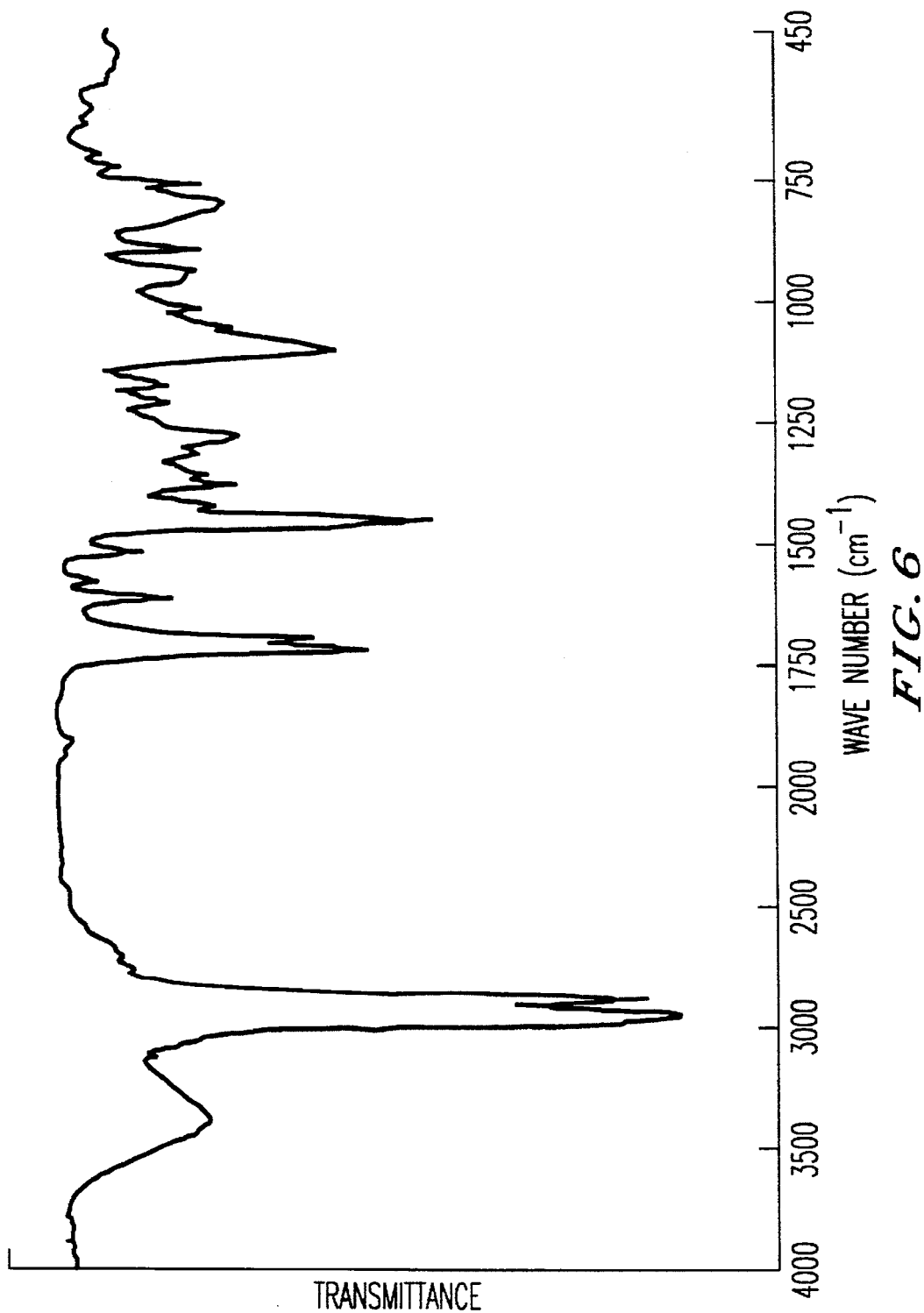
FIG. 6 is a diagram showing an infrared absorption spectrum of trans-4-(trans-4-butylcyclohexyl)cyclohexyl-4-propylbenzyl ether of the present invention.

This compound is a smectic liquid crystal, and had a C-S point of 45° C. and a S-I point of 106° C. Also, an infrared absorption spectrum of the compound is shown in FIG. 6.

Example 7

In the same manner as in Example 5 except for using 3.78 g of trans-4-(trans-4-pentylcyclohexyl)cyclohexanol in place of 3.36 g of trans-4-(trans-4-propylcyclohexyl)cyclohexanol, 2.0 g of trans-4-(trans-4-pentylcyclohexyl)cyclohexyl-4-propylbenzyl ether was obtained.

Figure 7:
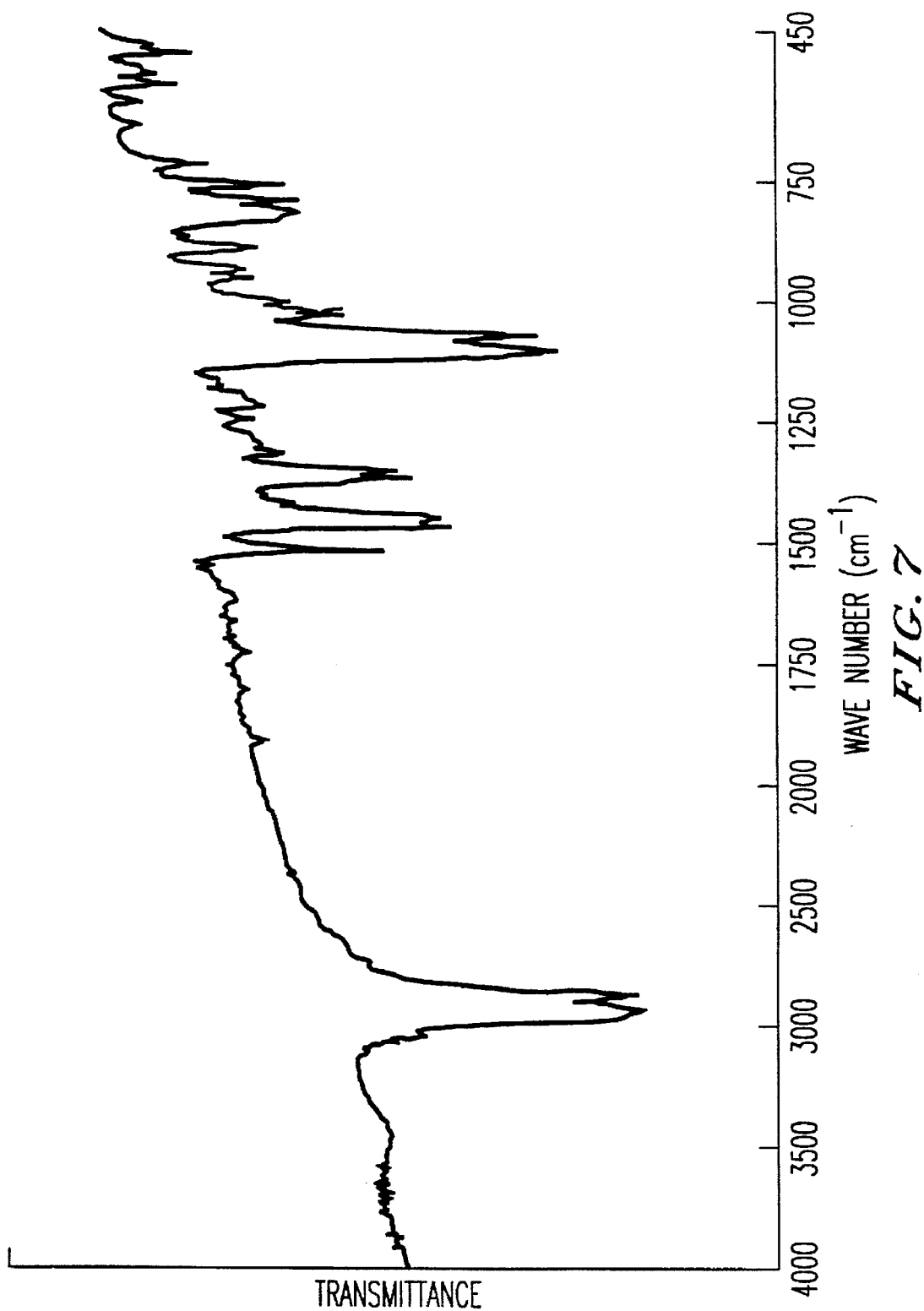
FIG. 7 is a diagram showing an infrared absorption spectrum of trans-4-(trans-4-pentylcyclohexyl)cyclohexyl-4-propylbenzyl ether of the present invention.

This compound is a smectic liquid crystal, and had a C-S point of 40° C. and a S-I point of 119° C. Also, an infrared absorption spectrum of the compound is shown in FIG. 7.

The following compounds can be obtained according to the same treatment.

Trans-4(trans-4-methylcyclohexyl)cyclohexyl-4-methylbenzyl ether

Trans-4(trans-4-methylcyclohexyl)cyclohexyl-4-propylbenzyl ether

Trans-4-(trans-4-methylcyclohexyl)cyclohexyl-4-pentylbenzyl ether

Trans-4-(trans-4-methylcyclohexyl)cyclohexyl4-heptylbenzyl ether

Trans-4-(trans-4-propylcyclohexyl)cyclohexyl-4-methylbenzyl ether

Trans-4-(trans-4-propylcyclohexyl)cyclohexyl-4-pentylbenzyl ether

Trans-4-(trans-4-propylcyclohexyl)cyclohexyl-4-heptylbenzyl ether

Trans-4-(trans-4-butylcyclohexyl)cyclohexyl-4-methylbenzyl ether

Trans-4-(trans-4-butylcyclohexyl)cyclohexyl-4-pentylbenzyl ether

Trans-4-(trans-4-butylcyclohexyl)cyclohexyl-4-butylbenzyl ether

Trans-4-(trans-4-pentylcyclohexyl)cyclohexyl-4-methylbenzyl ether

Trans-4-(trans-4-pentylcyclohexyl)cyclohexyl-4-pentylbenzyl ether

Trans-4-(trans-4-pentylcyclohexyl)cyclohexyl-4-heptylbenzyl ether

Trans-4-(trans-4-heptylcyclohexyl)cyclohexyl-4-methylbenzyl ether

Trans-4-(trans-4-heptylcyclohexyl)cyclohexyl-4-propylbenzyl ether

Trans-4-(trans-4-heptylcyclohexyl)cyclohexyl-4-pentylbenzyl ether

Trans-4-(trans-4-heptylcyclohexyl)cyclohexyl-4-heptylbenzyl ether

Example 8

To 90 parts by weight of the same base liquid crystal composition (ZLI-1083 available from Merck Co.) as in Example 3 was added 10 parts by weight of trans-4-(trans-4-propylcyclohexyl)cyclohexyl-4-propylbenzyl ether obtained in Example 5 to obtain a liquid crystal composition. While the characteristics of the base liquid crystal composition were a N-I point of 52° C., Δn of 0.12, a viscosity of 23.0 cp and Vth of 1.56 V, the resulting liquid crystal composition had a N-I point of 57° C., Δn of 0.114, a viscosity of 24.1 cP and Vth of 1.56 V.

Example 9

To 90 parts by weight of the same base liquid crystal composition used in Example 8 was added 10 parts by weight of trans-4-(trans-4-butylcyclohexyl)cyclohexyl-4-propylbenzyl ether obtained in Example 6 to obtain a liquid crystal composition. This liquid crystal composition had a N-I point of 57° C., Δn of 0.114, a viscosity of 23.3 cP and Vth of 1.56 V.

Example 10

To 90 parts by weight of the same base liquid crystal composition used in Example 8 was added 10 parts by weight of trans-4-(trans-4-pentylcyclohexyl)cyclohexyl-4-propylbenzyl ether obtained in Example 7 to obtain a liquid crystal composition. This liquid crystal composition had a N-I point of 58° C., Δn of 0.114, a viscosity of 23.5 cP and Vth of 1.53 V.

Example 11

The characteristics of the base liquid crystal composition prepared by mixing three kinds of compounds shown by the following formulae with a weight ratio of 1:1:1 were a N-I point of 71° C., Δn of 0.085 and a viscosity of 22.3 cP. To 90 parts by weight of this base liquid crystal composition was added 10 parts by weight of trans-4-(trans-4-propylcyclohexyl)cyclohexyl-4-propylbenzyl ether obtained in Example 5 to obtain a liquid crystal composition. This liquid crystal composition had a N-I point of 72° C., Δn of 0.084 and a viscosity of 23.0 cP.

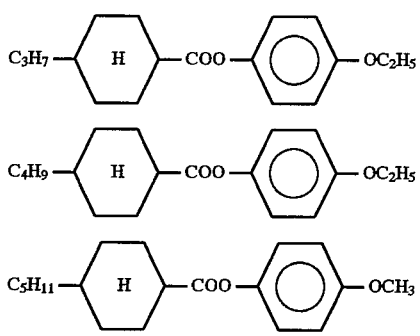

Example 12

To 90 parts by weight of the same base liquid crystal composition used in Example 11 was added 10 parts by weight of trans-4-(trans-4-butylcyclohexyl)cyclohexyl-4-propylbenzyl ether obtained in Example 6 to obtain a liquid crystal composition. This liquid crystal composition had a N-I point of 72° C., Δn of 0.084 and a viscosity of 23.9 cp.

Example 13

To 90 parts by weight of the same base liquid crystal composition used in Example 11 was added 10 parts by weight of trans-4-(trans-4-pentylcyclohexyl)cyclohexyl-4-propylbenzyl ether obtained in Example 7 to obtain a liquid crystal composition. This liquid crystal composition had a N-I point of 73° C., Δn of 0.084 and a viscosity of 23.1 cP.

Example 14

To 0.6 g of sodium hydride (purity 60%) was added 30 ml of anhydrous N,N-dimethylformamide. While stirring sufficiently, to the solution was added a solution of 3.36 g of trans-4-(trans-4-propylcyclohexyl)cyclohexanol dissolved in 10 ml of anhydrous N,N-dimethylformamide. This mixture was continued to stirring at 50° C. for one hour and then 2.8 g of 4-methoxybenzyl chloride was added thereto, and the mixture was stirred and reacted at the same temperature for 3 hours with stirring. After completion of the reaction, 100 ml of water was added to the reaction mixture, the mixture was extracted with toluene, washed with a saturated NaCl aqua, dried and the solvent was removed under reduced pressure. The residue was purified by silica gel column to obtain 1.0 g of the targeted trans-4-(trans-4-propylcyclohexyl)cyclohexyl-4-methoxybenzyl ether.

Figure 8:
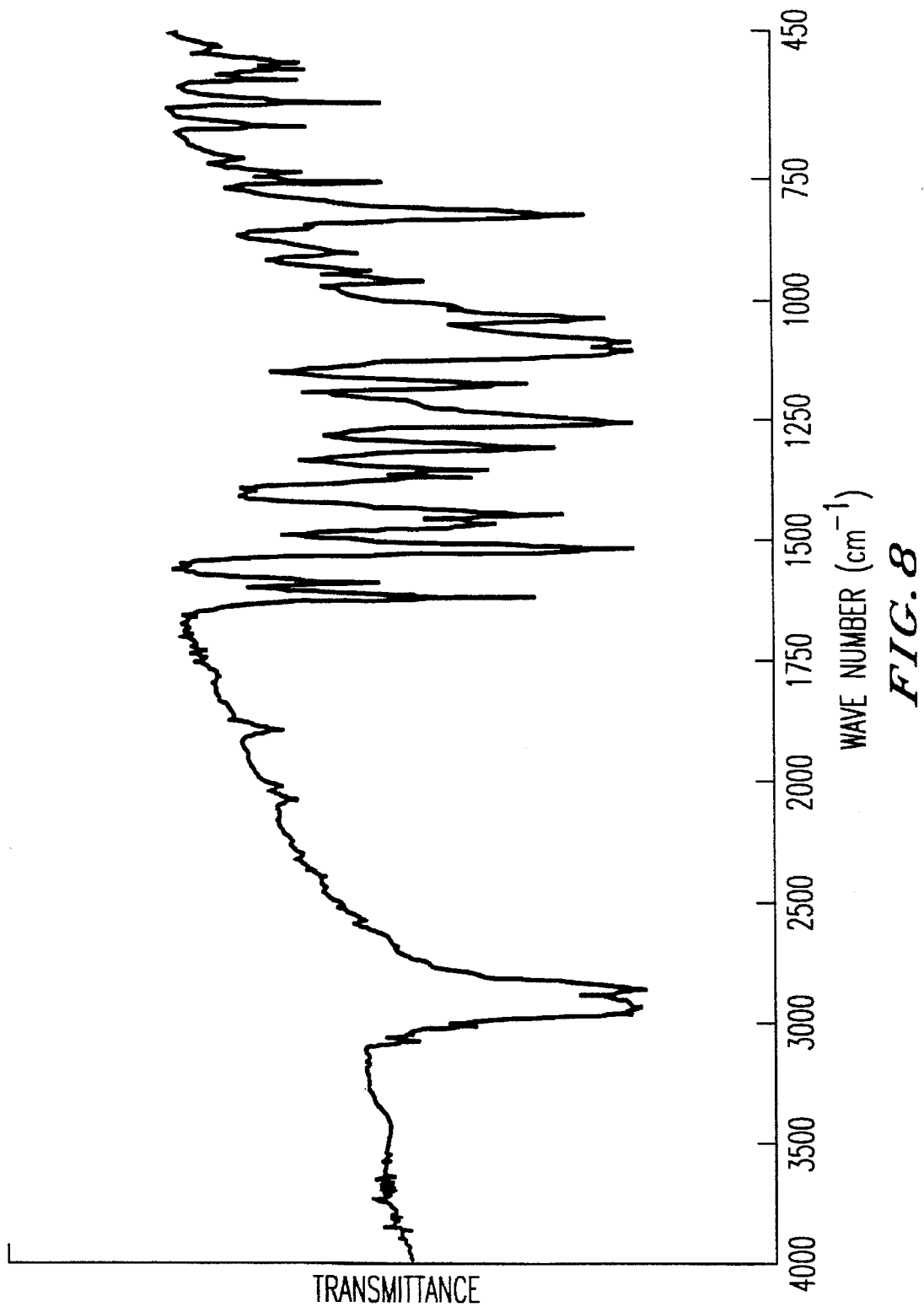
FIG. 8 is a diagram showing an infrared absorption spectrum of trans-4-(trans-4-propylcyclohexyl)cyclohexyl-4-methoxybenzyl ether of the present invention.

The resulting compound is a liquid crystal and had a C-S point (crystal-smectic point) of 45° C., a S-N point (smectic-nematic point) of 57° C. and a N-I point (nematic-isotropic liquid point) of 117° C. Also, the structure of the compound was confirmed by a mass spectrum and an infrared absorption spectrum. The resulting infrared absorption spectrum is shown in FIG. 8.

Example 15

In the same manner as in Example 14 except for using 3.57 g of trans-4-(trans-4-butylcyclohexyl)cyclohexanol in place of 3.36 g of trans-4-(trans-4-propylcyclohexyl) cyclohexanol, 1.5 g of trans-4-(trans-4-butylcyclohexyl) cyclohexyl-4-methoxybenzyl ether was obtained.

Figure 9:
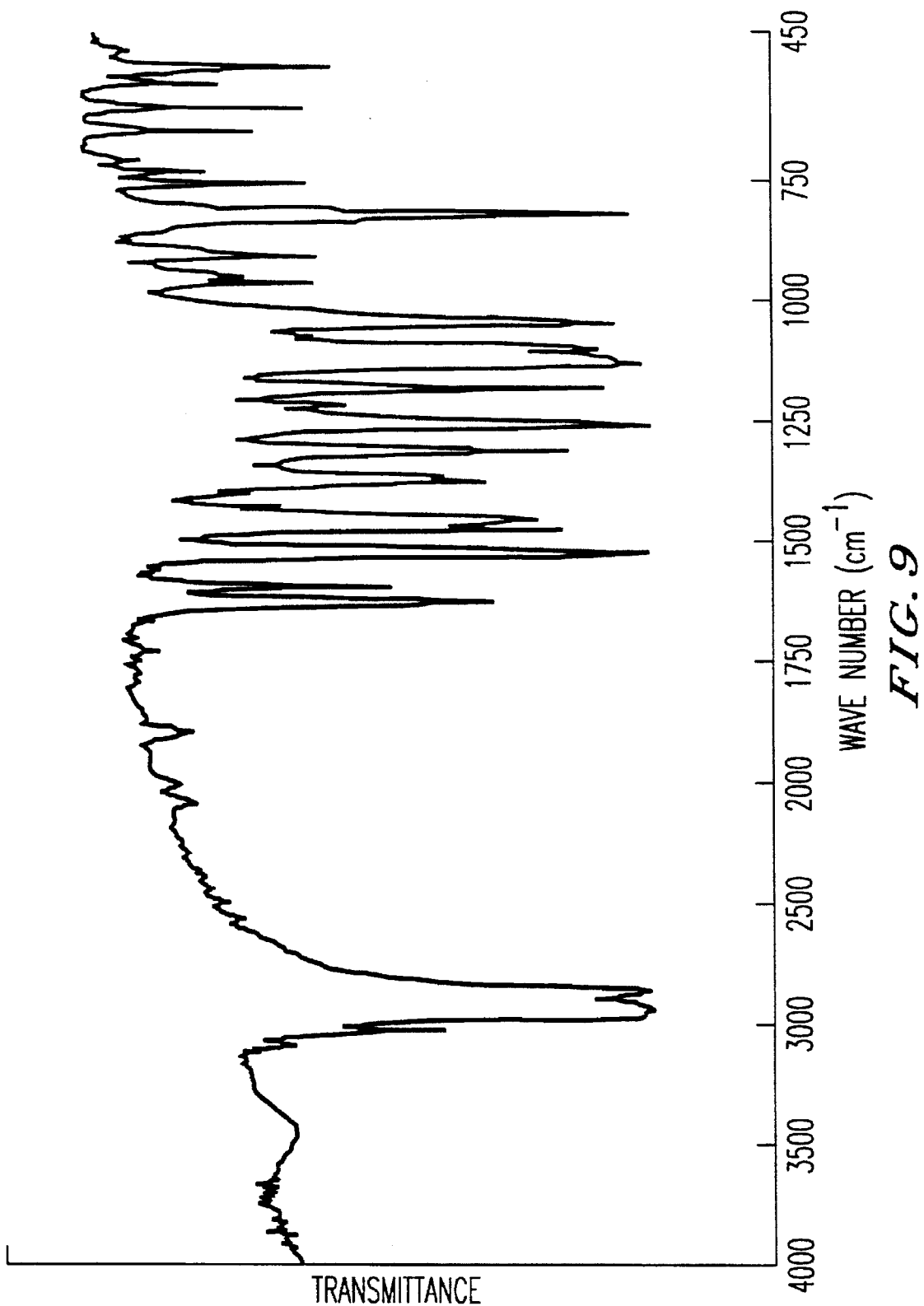
FIG. 9 is a diagram showing an infrared absorption spectrum of trans-4-(trans-4-butylcyclohexyl)cyclohexyl-4-methoxybenzyl ether of the present invention.

This compound is a liquid crystal, and had a C-S point of 56° C., a S-N point of 89° C. and a N-I point of 119° C. Also, the structure of the compound was confirmed by a mass spectrum and an infrared absorption spectrum. The resulting infrared absorption spectrum is shown in FIG. 9.

Example 16

In the same manner as in Example 14 except for using 3.78 g of trans-4-(trans-4-pentylcyclohexyl)cyclohexanol in place of 3.36 g of trans-4-(trans-4-propylcyclohexyl) cyclohexanol, 1.7 g of trans-4-(trans-4-pentylcyclohexyl) cyclohexyl-4-methoxybenzyl ether was obtained.

Figure 10:
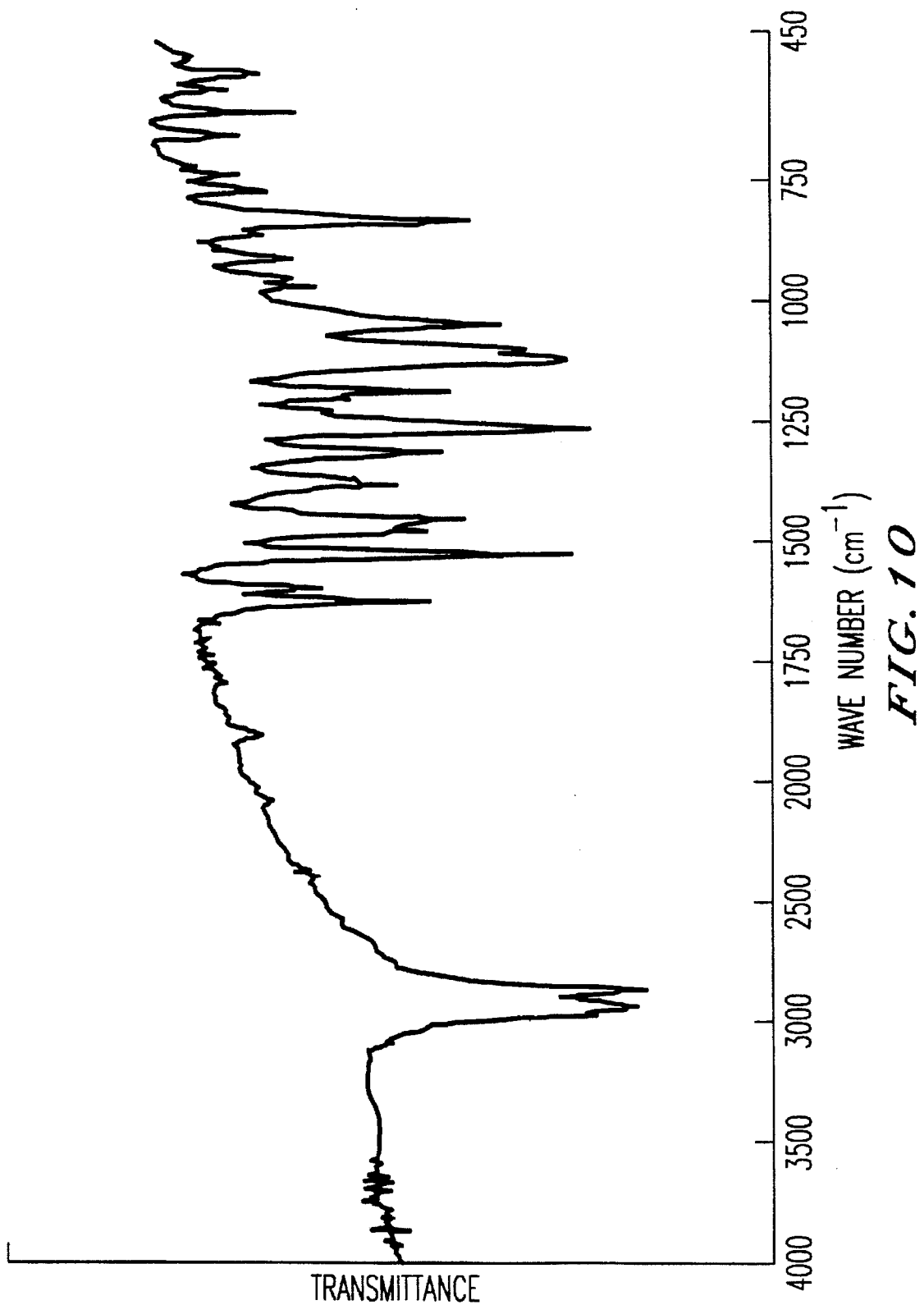
FIG. 10 is a diagram showing an infrared absorption spectrum of trans-4-(trans-4-pentylcyclohexyl)cyclohexyl-4-methoxybenzyl ether of the present invention.

This compound is a liquid crystal, and had a C-S point of 71° C., a S-N point of 89° C. and a N-I point of 119° C. Also, the structure of the compound was confirmed by a mass spectrum and an infrared absorption spectrum. The resulting infrared absorption spectrum is shown in FIG. 10.

The following compounds can be obtained according to the same treatment.

Trans-4(trans-4-methylcyclohexyl)cyclohexyl-4-methoxybenzyl ether

Trans-4(trans-4-ethylcyclohexyl)cyclohexyl-4-methoxybenzyl ether

Trans-4-(trans-4-hexylcyclohexyl)cyclohexyl-4-methoxybenzyl ether

Trans-4-(trans-4-heptylcyclohexyl)cyclohexyl-4-4-methoxybenzyl ether

Trans-4-(trans-4-propylcyclohexyl)cyclohexyl-4-ethoxybenzyl ether

Trans-4-(trans-4-propylcyclohexyl)cyclohexyl-4-propoxybenzyl ether

Trans-4-(trans-4-butylcyclohexyl)cyclohexyl-4-ethoxybenzyl ether

Trans-4-(trans-4-butylcyclohexyl)cyclohexyl-4-propoxybenzyl ether

Trans-4-(trans-4-pentylcyclohexyl)cyclohexyl-4-ethoxybenzyl ether

Trans-4-(trans-4-pentylcyclohexyl)cyclohexyl-4-propoxybenzyl ether

Example 17

To 90 parts by weight of the same base liquid crystal composition (ZLI-1083 available from Merck Co.) as in Example 3 was added 10 parts by weight of trans-4-(trans-4-propylcyclohexyl)cyclohexyl-4-methoxybenzyl ether obtained in Example 14 to obtain a liquid crystal composition. While the characteristics of the base liquid crystal composition were a N-I point of 52° C., Δn of 0.12, a viscosity of 23.0 cP and Vth of 1.51 V, the resulting liquid crystal composition had a N-I point of 61° C., Δn of 0.118, a viscosity of 23.7 cP and Vth of 1.57 V.

Example 18

To 90 parts by weight of the base liquid crystal composition used in Example 17 was added 10 parts by weight of trans-4-(trans-4-butylcyclohexyl)cyclohexyl-4-methoxybenzyl ether obtained in Example 15 to obtain a liquid crystal composition. This liquid crystal composition had a N-I point of 60° C., Δn of 0.117, a viscosity of 23.6 cP and Vth of 1.58 V.

Example 19

To 90 parts by weight of the base liquid crystal composition used in Example 17 was added 10 parts by weight of trans-4-(trans-4-pentylcyclohexyl)cyclohexyl-4-methoxybenzyl ether obtained in Example 16 to obtain a liquid crystal composition. This liquid crystal composition had a N-I point of 61° C., Δn of 0.117, a viscosity of 23.9 cP and Vth of 1.61 V.

Example 20

To one liter of dichloromethane were added 191 g of 3,4-difluorobiphenyl and 160 g of aluminum chloride, and maintaining the temperature to about 20° C., 86 g of acetyl chloride was gradually added dropwise under stirring. After completion of the dropwise addition, stirring was continued for 10 hours, and then 100 ml of hydrochloric acid was added to the mixture and the mixture was stirred well and washed. The mixture was further washed with water and the solvent was removed under reduced pressure. The residue was purified by distillation under reduced pressure (164° C./1 mmHg) to obtain 250 g of 3,4-difluoro-4-acetylbiphenyl.

Next, to a mixture in which 530 g of ice and 125 g of water were added to 126 g of sodium hydroxide was gradually added dropwise 125 g of bromine. After completion of dropwise addition, a solution of the previously obtained 45 g of 3,4-difluoro-4'-acetylbiphenyl dissolved in 230 ml of dioxane was added dropwise to the mixture at a temperature of 20° C. or lower. After completion of the dropwise addition, the mixture was heated to 50° C. and reacted for 1 hour. After the reaction, 100 ml of a 40% aqueous sodium bisulfite solution was added to precipitate crystals. The crystals were collected by filtration, washed well with methanol and purified by recrystallization to obtain 36 g of 3,4-difluorobiphenyl carboxylic acid.

To 30 g of the resulting 3,4-difluorobiphenyl carboxylic acid was added 400 ml of methanol, and under stirring, 10 g of sulfuric acid was added dropwise to the mixture. After completion of the dropwise addition, the mixture was refluxed and reacted for 2 hours. After completion of the reaction, the reaction mixture was cooled, 2 liters of water were added, and the mixture was extracted with toluene and washed with a saturated NaCl aqua, dried, and the solvent was removed under reduced pressure to obtain 31 g of a crude product of methyl 3,4-difluorobiphenyl carboxylate.

Next, to a solution comprising 4 g of lithium aluminum hydride dissolved in 200 ml of tetrahydrofuran was added dropwise a solution comprising 30 g of the previously obtained methyl 3,4-difluorobiphenyl carboxylate and 100 ml of tetrahydrofuran with stirring at −10° C., and the mixture was stirred for one hour at the same temperature to proceed the reaction. After completion of the reaction, to the reaction mixture was added 30 g of sulfuric acid and the resulting mixture was extracted with toluene. The reaction mixture was washed with a saturated NaCl aqua, dried, and the solvent was removed under reduced pressure. The residue was purified by distillation under reduced pressure (165° C/1 mmHg) to obtain 28 g of 4-(3,4-difluorophenyl)benzyl alcohol.

Next, to a solution comprising 25 g of the previously obtained 4-(3,4-difluorophenyl)benzyl alcohol, 40 g of triphenylphosphine and 80 ml of dichloromethane was added dropwise a solution comprising 64 g of carbon tetrabromide and 35 ml of dichloromethane under stirring at 0° C. After completion of the dropwise addition, the mixture was stirred at the same conditions for one hour, and then raised to room temperature and stirred for one hour to react the materials. After completion of the reaction, the reaction mixture was extracted with hexane, washed with a saturated NaCl aqua, dried and the solvent was removed under reduced pressure, and the residue was purified by recrystallization to obtain 20 g of 4-(3,4-difluorophenyl)benzyl bromide.

Next, a coupling reaction of an alcohol and benzyl bromide was carried out. To 40 ml of anhydrous tetrahydrofuran was added 0.8 g of sodium hydride (purity 60%). While vigorously stirring, to the solution were added a solution of 2.24 g of trans-4-(trans-4-propylcyclohexyl)cyclohexanol dissolved in 25 ml of anhydrous tetrahydrofuran and a solution of 3.4 g of the previously obtained 4-(3,4-difluorophenyl)benzyl bromide dissolved in 15 ml of anhydrous tetrahydrofuran. The mixture was refluxed while stirring for 12 hours to effect the reaction. After completion of the reaction, the reaction mixture was cooled, 5 ml of hydrochloric acid was added and the mixture was extracted with toluene, washed with a saturated NaCl aqua, dried and the solvent was removed under reduced pressure. The residue was purified by recrystallization to obtain 2.5 g of trans-4-(trans-4-propylcyclohexyl)cyclohexyl-4-(3,4-difluorophenyl)benzyl ether.

Figure 11:
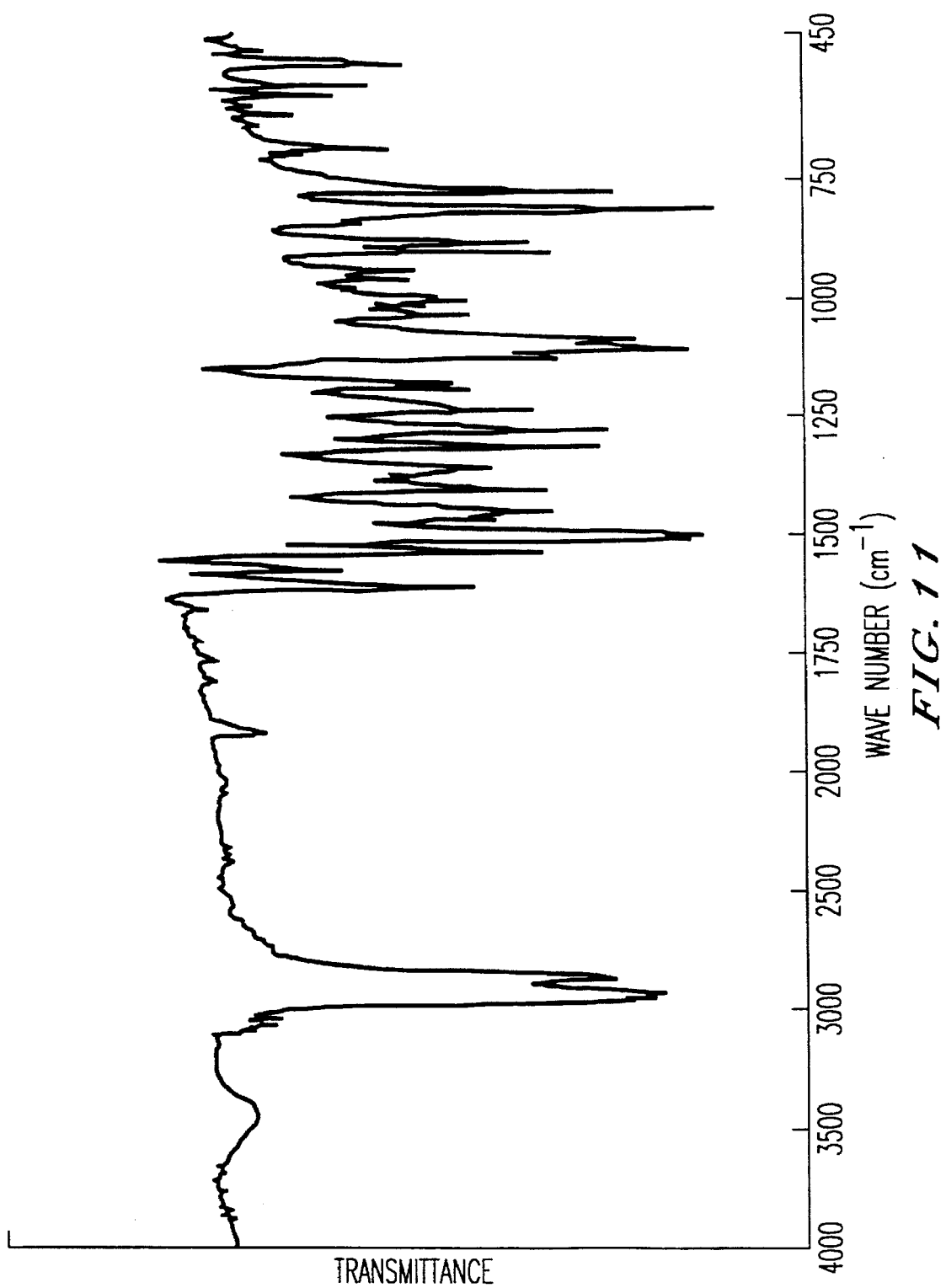
FIG. 11 is a diagram showing an infrared absorption spectrum of trans-4-(trans-4-propylcyclohexyl)cyclohexyl-4-(3,4-difluorophenyl)benzyl ether of the present invention.

This compound is a nematic liquid crystal, and had a C-N point of 109° C. and a N-I point of 182° C. Also, an infrared absorption spectrum of the compound was measured. The resulting infrared absorption spectrum is shown in FIG. 11.

Example 21

In the same manner as in Example 20 except for using 2.38 g of trans-4-(trans-4-butylcyclohexyl)cyclohexanol in place of 2.24 g of trans-4(trans-4-propylcyclohexyl) cyclohexanol, 2.4 g of trans-4-(trans-4-butylcyclohexyl) cyclohexyl-4-(3,4-difluorophenyl)benzyl ether was obtained.

Figure 12:
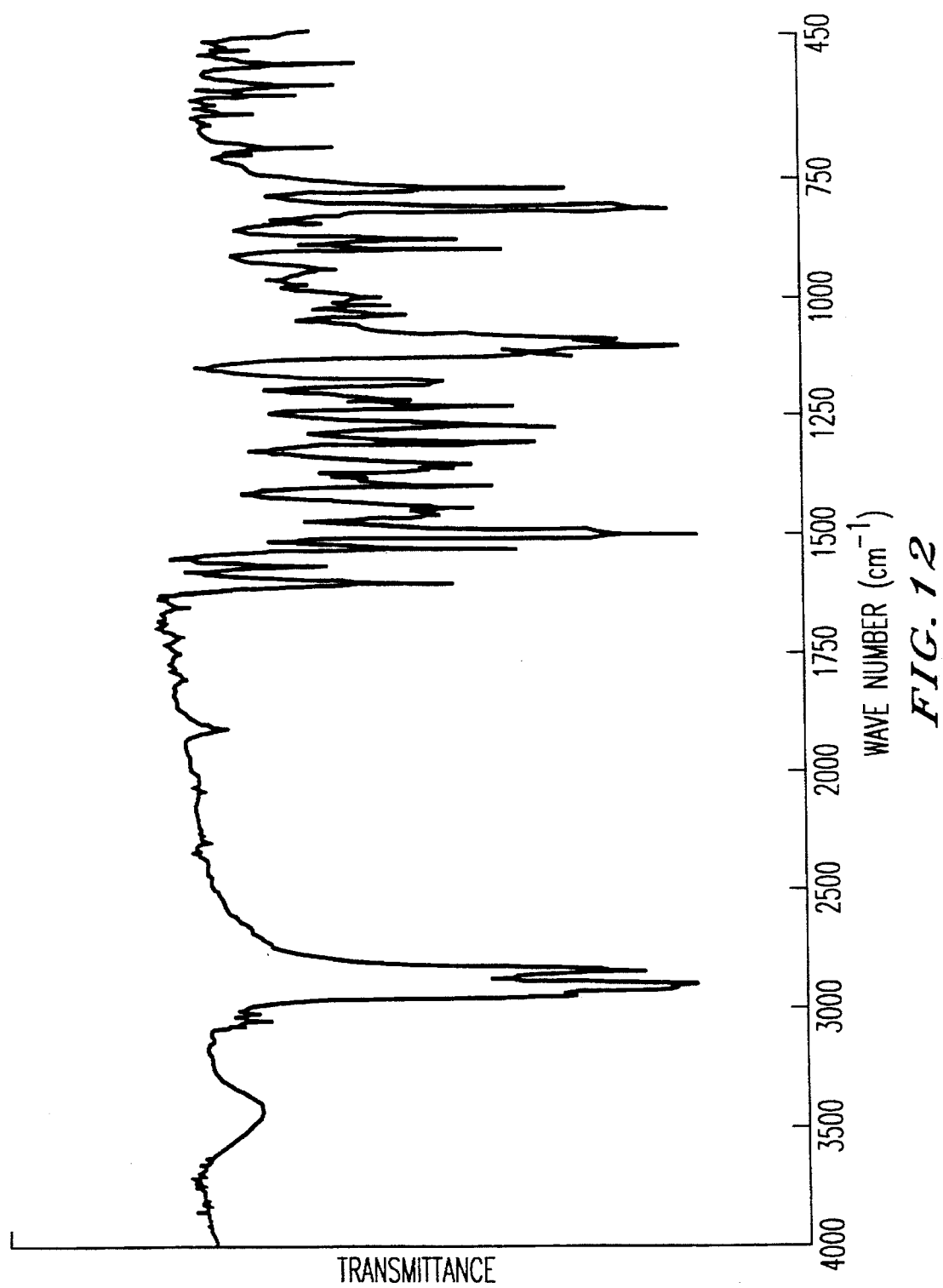
FIG. 12 is a diagram showing an infrared absorption spectrum of trans-4-(trans-4-butylcyclohexyl)cyclohexyl-4-(3,4-difluorophenyl)benzyl ether of the present invention.

This compound is a liquid crystal, and had a C-S point (crystal-smectic transfer point) of 82° C., a S-N point (smectic-nematic transfer point) of 97° C. and a N-I point of 178° C. Also, an infrared absorption spectrum of the compound is shown in FIG. 12.

Example 22

In the same manner as in Example 20 except for using 2.52 g of trans-4-(trans-4-pentylcyclohexyl)cyclohexanol in place of 2.24 g of trans-4-(trans-4-propylcyclohexyl) cyclohexanol, 2.7 g of trans-4-(trans-4-pentylcyclohexyl) cyclohexyl-4-(3,4-difluorophenyl)benzyl ether was obtained.

Figure 13:
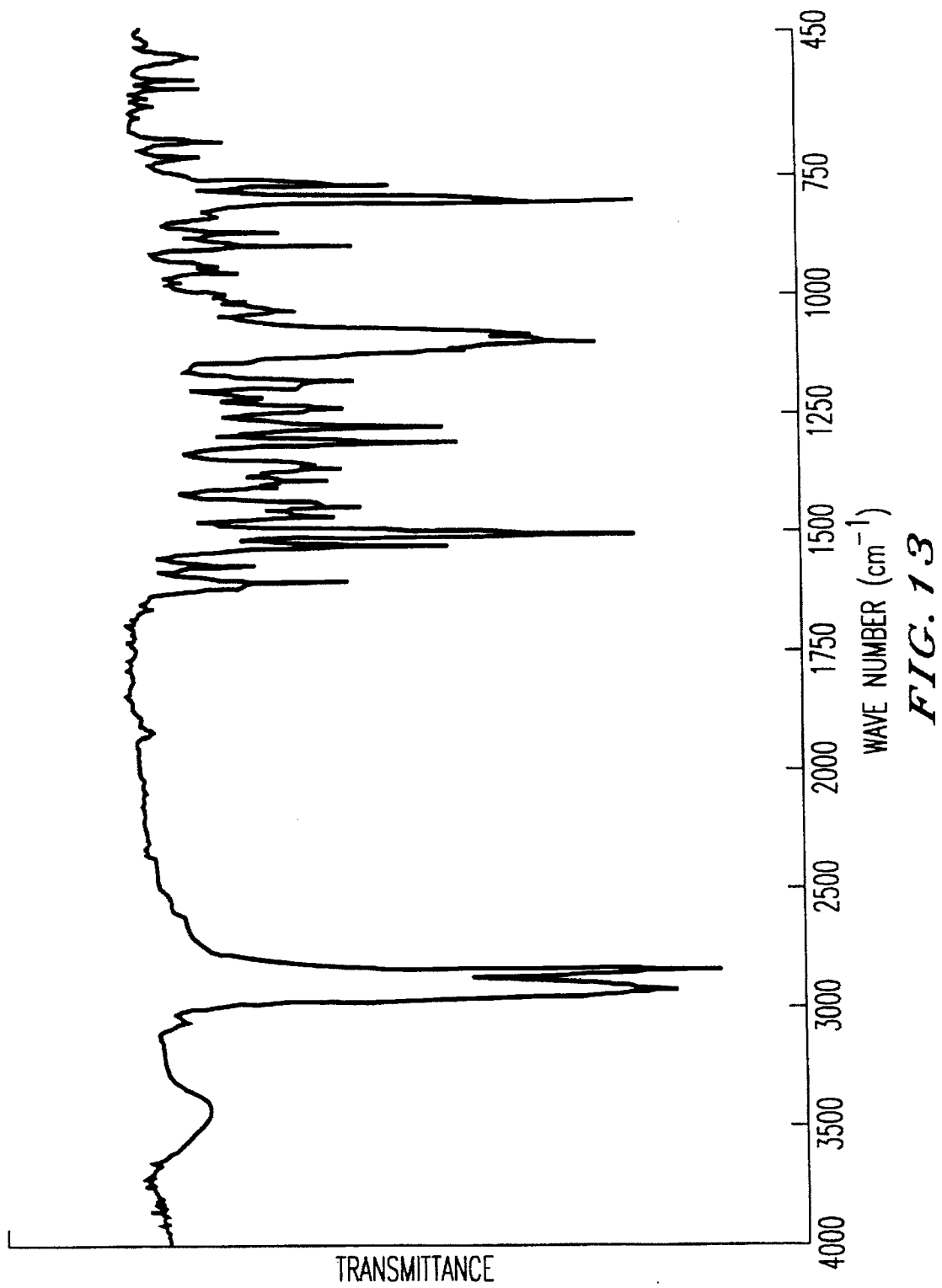
FIG. 13 is a diagram showing an infrared absorption spectrum of trans-4-(trans-4-pentylcyclohexyl)cyclohexyl-4-(3,4-difluorophenyl)benzyl ether of the present invention.

This compound is a nematic liquid crystal, and had a C-N point of 89° C. and a N-I point of 178° C. Also, an infrared absorption spectrum of the compound is shown in FIG. 13.

The following compounds can be obtained according to the same treatment.

Trans-4-(trans-4-methylcyclohexyl)cyclohexyl-4-(3,4) difluorophenyl)benzyl ether Trans-4-(trans-4-ethylcyclohexyl)cyclohexyl-4-(3,4-difluorophenyl)benzyl ether Trans-4-(trans-4-hexylcyclohexyl)cyclohexyl-4-(3,4-difluorophenyl)benzyl ether Trans-4-(trans-4-heptylcyclohexyl)cyclohexyl-4-(3,4-difluorophenyl)benzyl ether Trans-4-(trans-4-octylcyclohexyl)cyclohexyl-4-(3,4-difluorophenyl)benzyl ether Trans-4-(trans-4-nonylcyclohexyl)cyclohexyl-4-(3,4-difluorophenyl)benzyl ether Trans-4-(trans-4-decylcyclohexyl)cyclohexyl-4-(3,4-difluorophenyl)benzyl ether

Example 23

In the same manner as in Example 20 except for using 1.42 g of trans-4-propylcyclohexanol in place of 2.24 g of trans-4-(trans-4-propylcyclohexyl)cyclohexanol, 1.4 g of trans-4-propylcyclohexyl-4-(3,4-difluorophenyl)benzyl ether was obtained.

Figure 14:
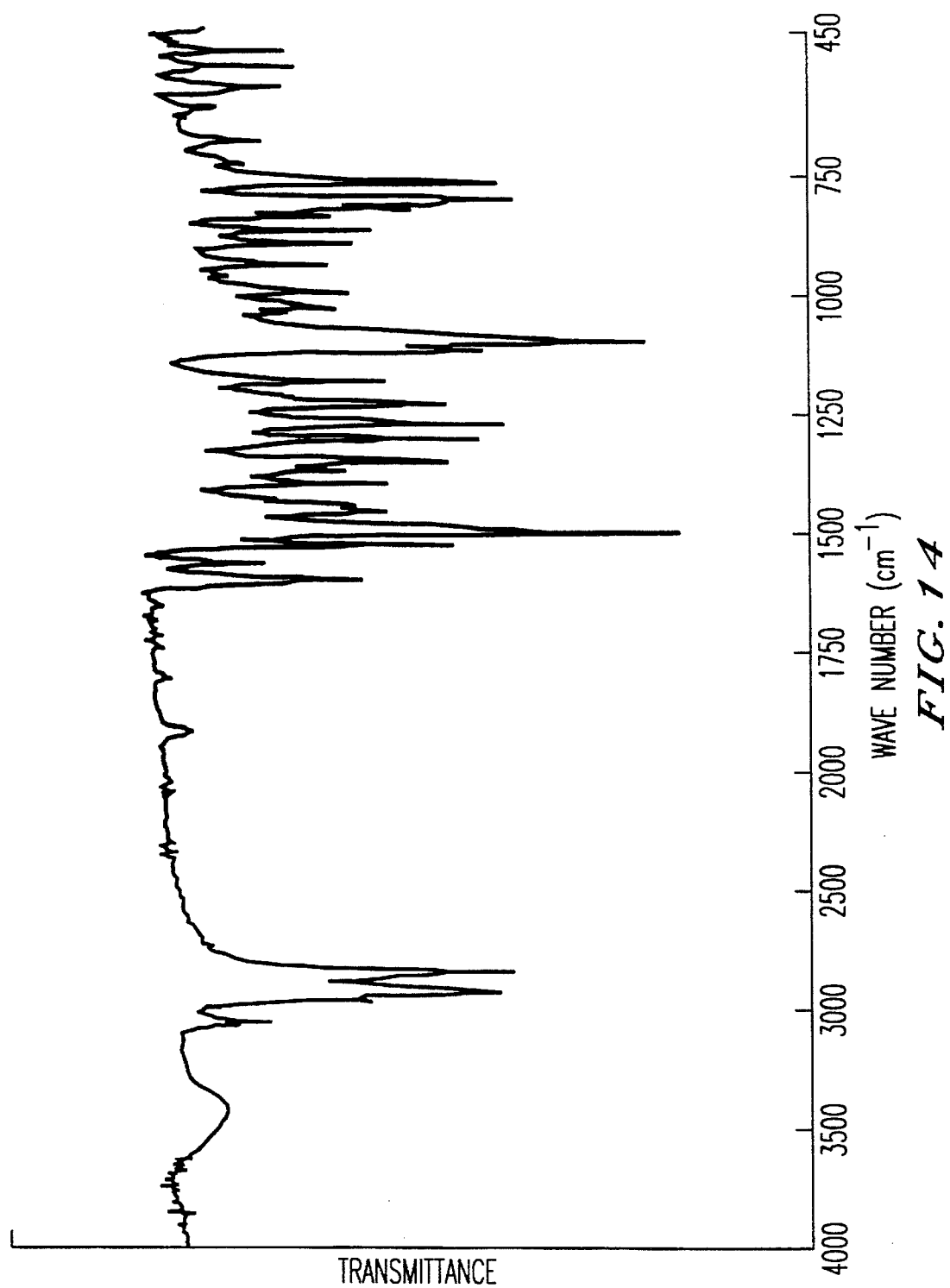
FIG. 14 is a diagram showing an infrared absorption spectrum of trans-4-propylcyclohexyl-4-(3,4-difluorophenyl)benzyl ether of the present invention.

This compound had a melting point of 71° C. Also, an infrared absorption spectrum of the compound is shown in FIG. 14.

Example 24

In the same manner as in Example 20 except for using 1.7 g of trans-4-pentylcyclohexanol in place of 2.24 g of trans-4-(trans-4-propylcyclohexyl)cyclohexanol, 1.6 g of trans-4-pentylcyclohexyl-4-(3,4-difluorophenyl)benzyl ether was obtained.

Figure 15:
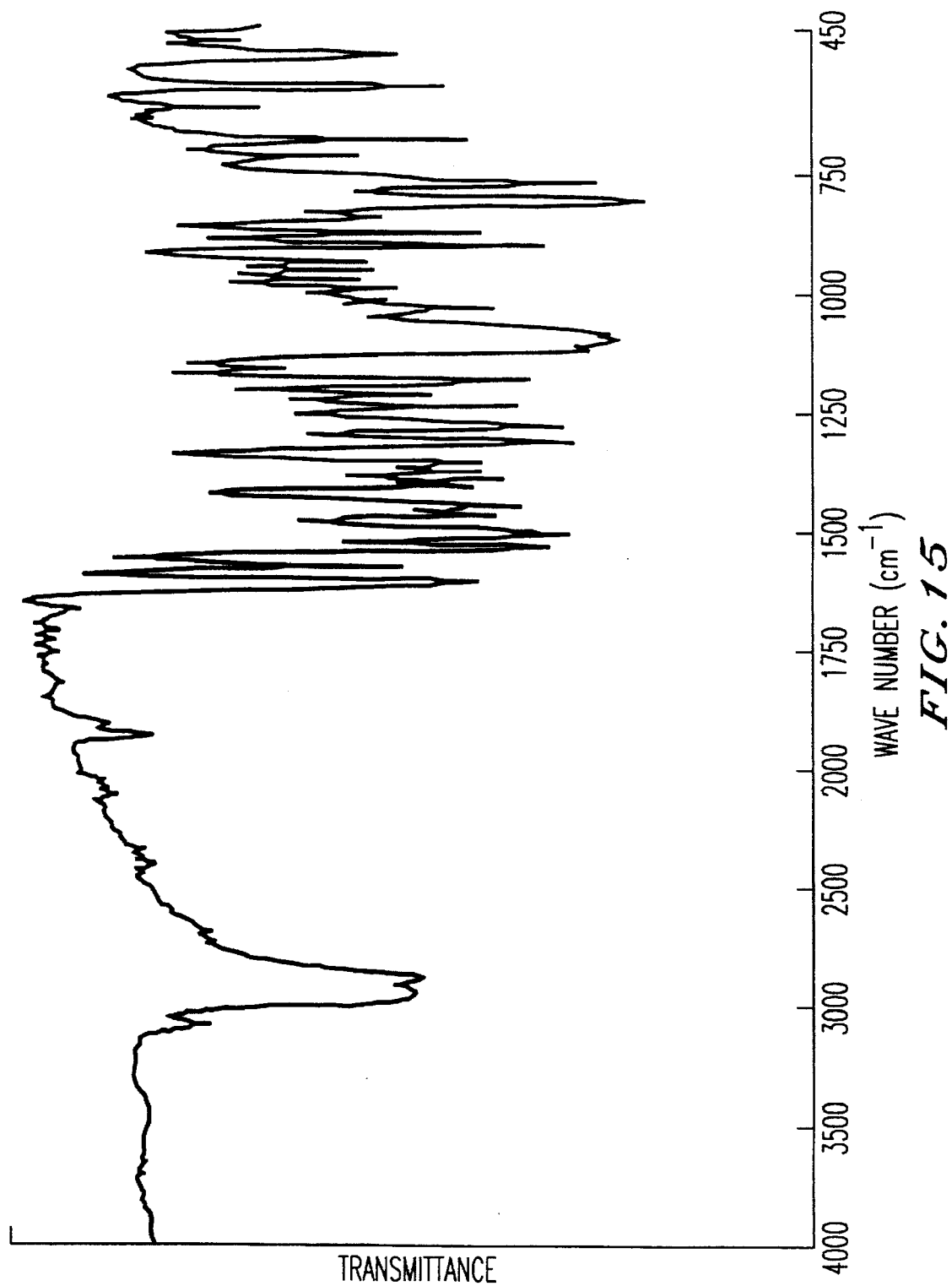
FIG. 15 is a diagram showing an infrared absorption spectrum of trans-4-pentylcyclohexyl-4-(3,4-difluorophenyl)benzyl ether of the present invention.

This compound is a monotropic liquid crystal, and had a melting point of 63° C. and a I-N point (isotropic liquid-nematic point) of 55° C. Also, an infrared absorption spectrum of the compound is shown in FIG. 15.

The following compounds can be obtained according to the same treatment.

Trans-4-methylcyclohexyl-4-(3,4-difluorophenyl)benzyl ether

Trans-4-ethylcyclohexyl-4-(3,4-difluorophenyl)benzyl ether

Trans-4-butylcyclohexyl-4-(3,4-difluorophenyl)benzyl ether

Trans-4-hexylcyclohexyl-4-(3,4-difluorophenyl)benzyl ether

Trans-4-heptylcyclohexyl-4-(3,4-difluorophenyl)benzyl ether

Trans-4-octylcyclohexyl-4-(3,4-difluorophenyl)benzyl ether

Trans-4-nonylcyclohexyl-4-(3,4-difluorophenyl)benzyl ether

Trans-4-decylcyclohexyl-4-(3,4-difluorophenyl)benzyl ether

Example 25

To 40 ml of anhydrous tetrahydrofuran was added 0.8 g of sodium hydride (purity 60%). While stirring sufficiently, to the solution were added a solution of 2.24 g of trans-4-(trans-4-propylcyclohexyl)cyclohexanol dissolved in 25 ml of anhydrous tetrahydrofuran and a solution of 2.4 g of commercially available 2,3-difluorobenzyl bromide dissolved in 15 ml of anhydrous tetrahydrofuran. This mixture was continued to reflux for 12 hours under stirring to effect a coupling reaction. After completion of the reaction, the reaction mixture was cooled, 5 ml of hydrochloric acid was added and the mixture was extracted with toluene, washed with a saturated NaCl aqua, dried and the solvent was removed under reduced pressure. The residue was purified by recrystallization to obtain 1.0 g of trans-4-(trans-4-propylcyclohexyl)cyclohexyl-2,3-difluorobenzyl ether.

Figure 16:
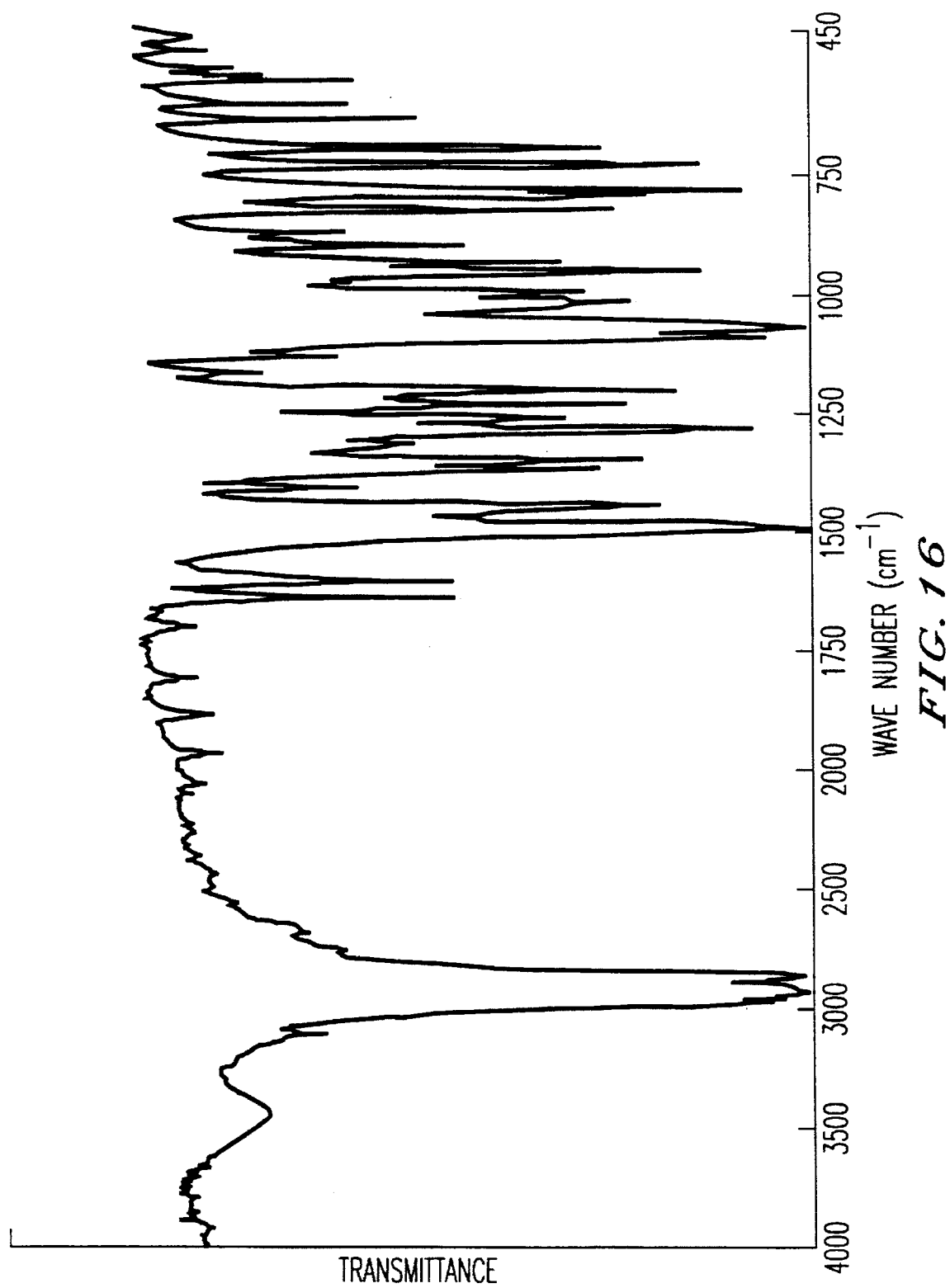
FIG. 16 is a diagram showing an infrared absorption spectrum of trans-4-(trans-4-propylcyclohexyl)cyclohexyl-2,3-difluorobenzyl ether of the present invention.

The resulting compound had a melting point of 69° C. Also, an infrared absorption spectrum of the compound is shown in FIG. 16.

The following compounds can be obtained according to the same treatment.

Trans-4-(trans-4-methylcyclohexyl)cyclohexyl-2,3-difluorobenzyl ether

Trans-4-(trans-4-ethylcyclohexyl)cyclohexyl-2,3-difluorobenzyl ether

Trans-4-(trans-4-butylcyclohexyl)cyclohexyl-2,3-difluorobenzyl ether

Trans-4-(trans-4-pentylcyclohexyl)cyclohexyl-2,3-difluorobenzyl ether

Trans-4-(trans-4-hexylcyclohexyl)cyclohexyl-2,3-difluorobenzyl ether

Trans-4-(trans-4-heptylcyclohexyl)cyclohexyl-2,3-difluorobenzyl ether

Trans-4-(trans-4-octylcyclohexyl)cyclohexyl-2,3-difluorobenzyl ether

Trans-4-(trans-4-nonylcyclohexyl)cyclohexyl-2,3-difluorobenzyl ether

Trans-4-(trans-4-decylcyclohexyl)cyclohexyl-2,3-difluorobenzyl ether

Example 26

In the same manner as in Example 25 except for using 2.7 g of commercially available 2,3,4-trifluorobenzyl bromide in place of 2.4 g of 2,3-difluorobenzyl bromide and using 2.52 g of trans-4-(trans-4-pentylcyclohexyl)cyclohexanol in place of 2.24 g of trans-4-(trans-4-propylcyclohexyl)cyclohexanol, 1.2 g of trans-4-(trans-4-pentylcyclohexyl)cyclohexyl-2,3,4-trifluorobenzyl ether was obtained.

Figure 17:
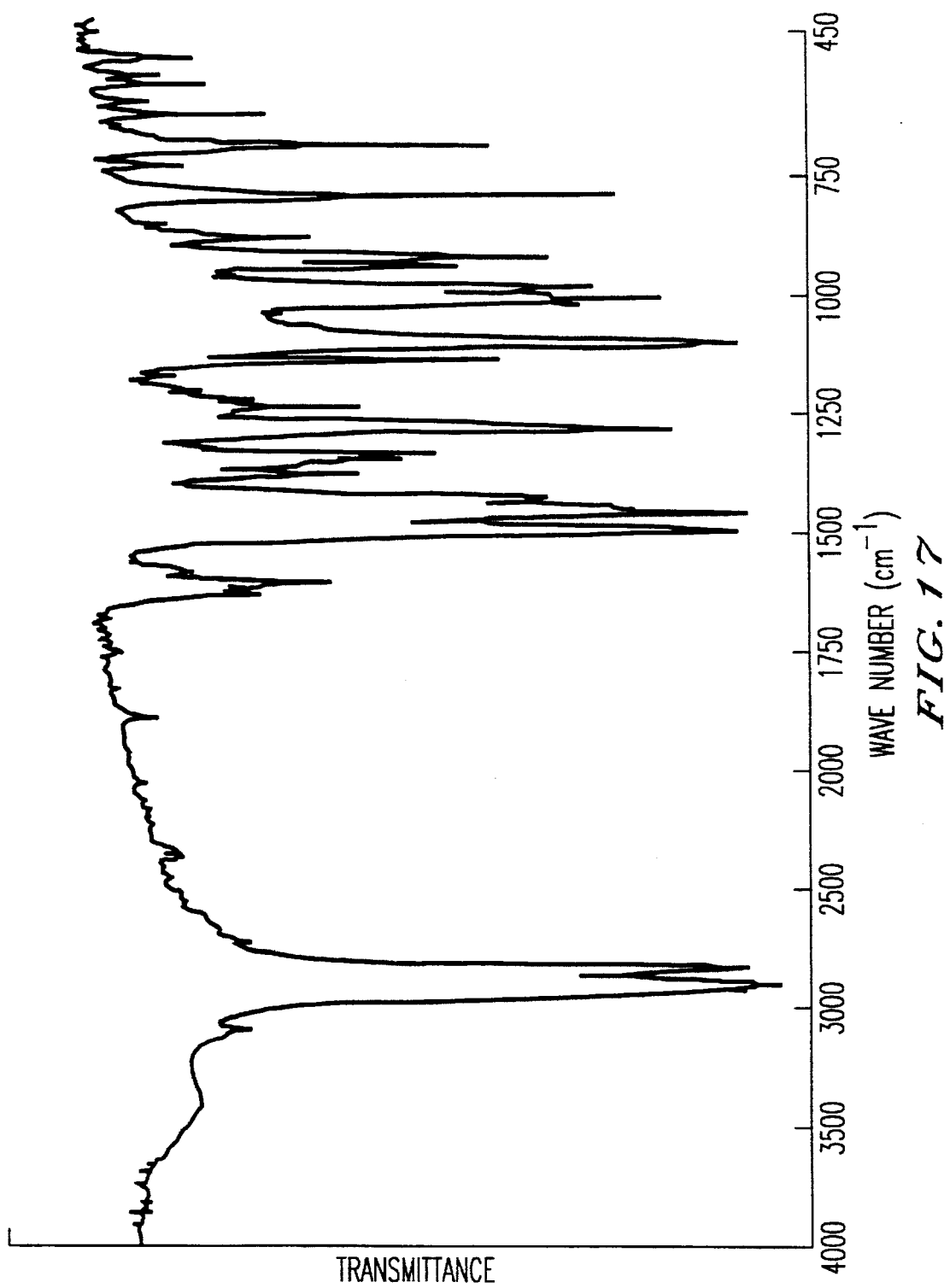
FIG. 17 is a diagram showing an infrared absorption spectrum of trans-4-(trans-4-pentylcyclohexyl)cyclohexyl-2,3,4-trifluorobenzyl ether of the present invention.

This compound had a melting point of 63° C. Also, an infrared absorption spectrum of the compound is shown in FIG. 17.

The following compounds can be obtained according to the same treatment.

Trans-4-(trans-4-methylcyclohexyl)cyclohexyl-2,3,4-trifluorobenzyl ether

Trans-4-(trans-4-ethylcyclohexyl)cyclohexyl-2,3,4-trifluorobenzyl ether

Trans-4-(trans-4-propylcyclohexyl)cyclohexyl-2,3,4-trifluorobenzyl ether

Trans-4-(trans-4-butylcyclohexyl)cyclohexyl-2,3,4-trifluorobenzyl ether

Trans-4-(trans-4-hexylcyclohexyl)cyclohexyl-2,3,4-trifluorobenzyl ether

Trans-4-(trans-4-heptylcyclohexyl)cyclohexyl-2,3,4-trifluorobenzyl ether

Trans-4-(trans-4-octylcyclohexyl)cyclohexyl-2,3,4-trifluorobenzyl ether

Trans-4-(trans-4-nonylcyclohexyl)cyclohexyl-2,3,4-trifluorobenzyl ether

Trans-4-(trans-4-decylcyclohexyl)cyclohexyl-2,3,4-trifluorobenzyl ether

Example 27

In the same manner as in Example 25 except for using 2.4 g of commercially available 2,4-difluorobenzyl bromide in place of 2.4 g of 2,3-difluorobenzyl bromide and using 2.52 g of trans-4-(trans-4-pentylcyclohexyl)cyclohexanol in place of 2.24 g of trans-4-(trans-4-propylcyclohexyl)cyclohexanol, 1.1 g of trans-4-(trans-4-pentylcyclohexyl)cyclohexyl-2,4-difluorobenzyl ether was obtained.

Figure 18:
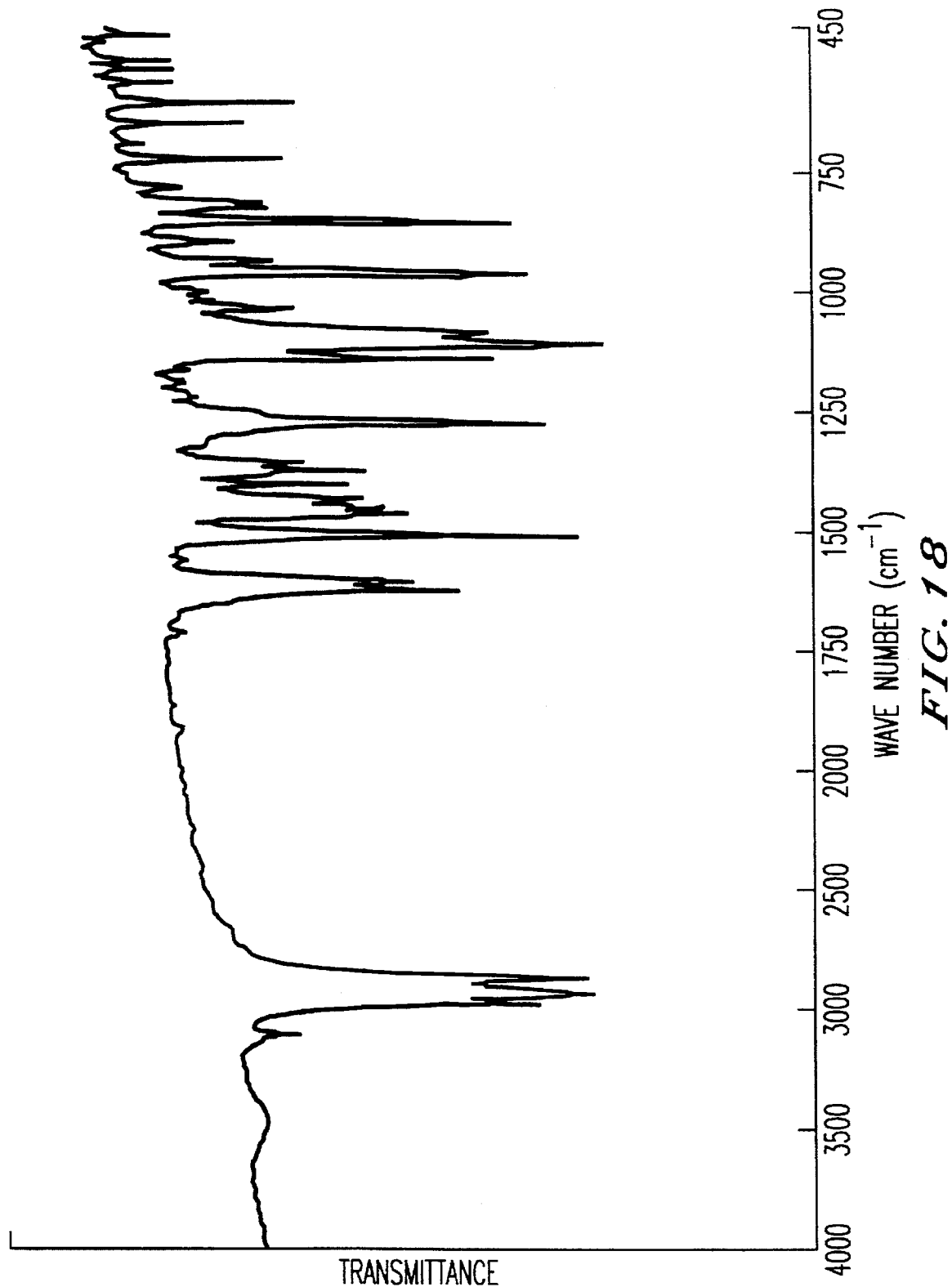
FIG. 18 is a diagram showing an infrared absorption spectrum of trans-4-(trans-4-pentylcyclohexyl)cyclohexyl-2,4-difluorobenzyl ether of the present invention.

This compound is a nematic liquid crystal, and had a C-N point of 56° C. and a N-I point of 85° C. Also, an infrared absorption spectrum of the compound is shown in FIG. 18.

The following compounds can be obtained according to the same treatment.

Trans-4-(trans-4-methylcyclohexyl)cyclohexyl-2,4-difluorobenzyl ether

Trans-4-(trans-4-ethylcyclohexyl)cyclohexyl-2,4-difluorobenzyl ether

Trans-4-(trans-4-propylcyclohexyl)cyclohexyl-2,4-difluorobenzyl ether

Trans-4-(trans-4-butylcyclohexyl)cyclohexyl-2,4-difluorobenzyl ether

Trans-4-(trans-4-hexylcyclohexyl)cyclohexyl-2,4-difluorobenzyl ether

Trans-4-(trans-4-heptylcyclohexyl)cyclohexyl-2,4-difluorobenzyl ether

Trans-4-(trans-4-octylcyclohexyl)cyclohexyl-2,4-difluorobenzyl ether

Trans-4-(trans-4-nonylcyclohexyl)cyclohexyl-2,4-difluorobenzyl ether

Trans-4-(trans-4-decylcyclohexyl)cyclohexyl-2,4-difluorobenzyl ether

Example 28

To 90 parts by weight of the same base liquid crystal composition (ZLI-1083 available from Merck Co.) as in Example 3 was added 10 parts by weight of trans-4-(trans-4-propylcyclohexyl)cyclohexyl-4-(3,4-difluorophenyl)benzyl ether obtained in Example 20 to obtain a liquid crystal composition. While the characteristics of the base liquid crystal composition were a N-I point of 52° C., Δn of 0.12, a viscosity of 23.0 cp and Vth of 1.51 V, the resulting liquid crystal composition had a N-I point of 64.8° C., Δn of 0.122, a viscosity of 26.5 cp and Vth of 1.64 V.

Example 29

To 90 parts by weight of the base liquid crystal composition used in Example 28 was added 10 parts by weight of trans-4-(trans-4-butylcyclohexyl)cyclohexyl-4-(3,4-difluorophenyl)benzyl ether obtained in Example 21 to obtain a liquid crystal composition. This liquid crystal composition had a N-I point of 54.0° C., Δn of 0.122, a viscosity of 26.9 cP and Vth of 1.64 V.

Example 30

To 90 parts by weight of the base liquid crystal composition used in Example 28 was added 10 parts by weight of trans-4-(trans-4-pentylcyclohexyl)cyclohexyl-4-(3,4-difluorophenyl)benzyl ether obtained in Example 22 to obtain a liquid crystal composition. This liquid crystal composition had a N-I point of 64.6° C., Δn of 0.122, a viscosity of 27.6 cP and Vth of 1.61 V.

Example 31

To 90 parts by weight of the base liquid crystal composition used in Example 28 was added 10 parts by weight of trans-4-propylcyclohexyl-4-(3,4-difluorophenyl)benzyl ether obtained in Example 23 to obtain a liquid crystal composition. This liquid crystal composition had a N-I point of 52.1° C., Δn of 0.117, a viscosity of 24.0 cP and Vth of 1.47 V.

Example 32

To 90 parts by weight of the base liquid crystal composition used in Example 28 was added 10 parts by weight of trans-4-pentylcyclohexyl-4-(3,4-difluorophenyl)benzyl ether obtained in Example 24 to obtain a liquid crystal composition. This liquid crystal composition had a N-I point of 53.0° C., Δn of 0.118, a viscosity of 24.8 cP and Vth of 1.49 V.

Example 33

To 90 parts by weight of the base liquid crystal composition used in Example 28 was added 10 parts by weight of trans-4-(trans-4-propylcyclohexyl)cyclohexyl-2,3-difluorobenzyl ether obtained in Example 25 to obtain a liquid crystal composition. This liquid crystal composition had a N-I point of 53.4° C., Δn of 0.114, a viscosity of 23.1 cP and Vth of 1.53 V.

Example 34

To 90 parts by weight of the base liquid crystal composition used in Example 28 was added 10 parts by weight of trans-4-(trans-4-pentylcyclohexyl)cyclohexyl-2,3,4-trifluorobenzyl ether obtained in Example 26 to obtain a liquid crystal composition. This liquid crystal composition had a N-I point of 53.0° C., Δn of 0.112, a viscosity of 24.1 cP and Vth of 1.46 V.

Example 35

To 90 parts by weight of the base liquid crystal composition used in Example 28 was added 10 parts by weight of trans-4-(trans-4-pentylcyclohexyl)cyclohexyl-2,4-difluorobenzyl ether obtained in Example 27 to obtain a liquid crystal composition. This liquid crystal composition had a N-I point of 55.6° C., Δn of 0.115, a viscosity of 23.6 cp and Vth of 1.61 V.

As shown in the above-mentioned Examples 3, 4 and 28–35, the fluorine-containing benzyl ether derivatives (Ia) of the present invention have effects of lowering the crystal-nematic starting point and the threshold voltage Vth or increasing the N-I point of a composition by formulating it in the liquid crystal composition. Also, depending on the compounds, they also have an effect of making Δn of the liquid crystal composition small or large.

Also, as shown in above-mentioned Examples 8–13 and Examples 17–19, the benzyl ether derivatives (Ib) of the present invention have an effect of increasing the N-I point of a composition by mixing in the liquid crystal composition.

Applicability in Industry

The compound (I) of the present invention has good compatibility with other compounds, and can be used in a liquid crystal composition by combining with many liquid crystal materials as a constitutional component of the liquid crystal composition. It has functions of lowering a C-N point of a liquid crystal composition, lowering a threshold voltage by enlarging a dielectric anisotropy, and also lowering a viscosity and increasing a N-I point of the liquid crystal composition as described above.

Further, by selecting the compound (I) of the present invention, it is also possible to change an optical anisotropy.

Accordingly, various properties of the compounds (I) of the present invention as described above can be utilized as a constitutional component of the liquid crystal composition by using with many liquid crystal materials in combination, and these compounds can be advantageously used for improving characteristics of a liquid crystal composition particularly for a TN type, STN type or active type liquid crystal display device.

We claim:

1. A benzyl ether having formula (I)

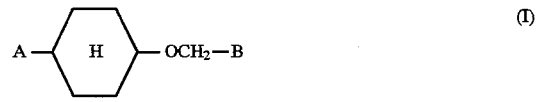

wherein

A is 4-$C_{1-10}$ alkylcyclohexyl, and B is difluorophenyl, trifluorophenyl, 4-(difluorophenyl)phenyl, 4-(trifluorophenyl)phenyl, 4-$C_{1-10}$ alkylphenyl or 4-$C_{1-10}$ alkoxyphenyl; or A is $C_{1-10}$ alkyl, and B is difluorophenyl, trifluorophenyl, 4-(difluorophenyl)phenyl or 4-(trifluorophenyl)phenyl.

2. The benzyl ether of claim 1, having formula (Ia)

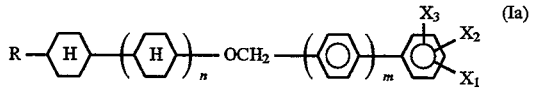

wherein R is $C_{1-10}$ alkyl, at least two of $X_1$, $X_2$ and $X_3$ are fluorine, and the remaining one of $X_1$, $X_2$ and $X_3$ is hydrogen or fluorine, and n and m are each an integer of 0 or 1.

3. The benzyl ether of claim 1, having formula (Ib)

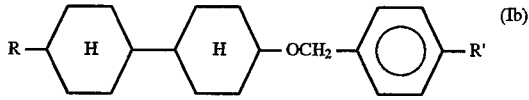

wherein R is $C_{1-10}$ alkyl and R' is $C_{1-10}$ alkyl or $C_{1-10}$ alkoxy.

4. The benzyl ether of claim 1, wherein A is 4-$C_{1-10}$ alkylcyclohexyl.

5. The benzyl ether of claim 1, wherein A is $C_{1-10}$ alkyl.

6. The benzyl ether of claim 4, wherein B is difluorophenyl, trifluorophenyl, 4-(difluorophenyl)phenyl or 4-(trifluorophenyl)phenyl.

7. A liquid crystal composition, comprising the benzyl ether of claim 1 and a liquid crystal compound different than said benzyl ether.

8. A liquid crystal composition, comprising a plurality of said benzyl ethers of claim 1.

9. The composition of claim 7, containing 5–80% by weight of said benzyl ether.

10. The composition of claim 9, containing 10–50% by weight of said benzyl ether.

11. A liquid crystal display device which carries a liquid crystal composition containing at least one of the benzyl ether of claim 1.

12. The benzyl ether of claim 1, wherein A is 4-$C_{1-7}$ alkylcyclohexyl.

13. The benzyl ether of claim 1, wherein B is 4-$C_{1-7}$ alkylphenyl.

14. The benzyl ether of claim 1, wherein A is 4-$C_{1-7}$ alkyl.

15. The benzyl ether of claim 1, wherein A is 4-propylcyclohexyl, 4-butylcyclohexyl or 4-pentylcyclohexyl.

16. The benzyl ether of claim 1, wherein A is propyl, butyl or pentyl.

17. The benzyl ether of claim 1, wherein B is 4-$C_{1-3}$ alkoxyphenyl.

* * * * *